(12) United States Patent  
Goldstein

(10) Patent No.: US 7,008,622 B2  
(45) Date of Patent: Mar. 7, 2006

(54) METHODS AND COMPOSITIONS FOR IMPAIRING MULTIPLICATION OF HIV-1

(75) Inventor: Gideon Goldstein, Short Hills, NJ (US)

(73) Assignee: Thymon, L.L.C., Short Hills, NJ (US)

( * ) Notice: Subject to any disclaimer, the term of this patent is extended or adjusted under 35 U.S.C. 154(b) by 332 days.

(21) Appl. No.: 10/086,208

(22) Filed: Feb. 28, 2002

(65) Prior Publication Data

US 2003/0194408 A1 Oct. 16, 2003

Related U.S. Application Data

(60) Division of application No. 09/451,067, filed on Nov. 30, 1999, now Pat. No. 6,525,179, which is a division of application No. 09/113,921, filed on Jul. 10, 1998, now Pat. No. 6,193,981, which is a continuation-in-part of application No. 08/893,853, filed on Jul. 11, 1997, now Pat. No. 5,871,994.

(51) Int. Cl.  
*A61K 39/42* (2006.01)

(52) U.S. Cl. .............. 424/139.1; 424/148.1; 424/160.1; 424/188.1; 424/208.1; 530/387.9; 530/388.35; 530/389.4

(58) Field of Classification Search ............ 530/388.35, 530/389.4; 424/188.1, 208.1, 190.1, 160.1

See application file for complete search history.

(56) References Cited

U.S. PATENT DOCUMENTS

| | | | |
|---|---|---|---|
| 4,871,488 A | 10/1989 | Mannino |
| 5,019,510 A | 5/1991 | Wain-Hobson |
| 5,110,802 A | 5/1992 | Cantin |
| 5,158,877 A | 10/1992 | Edwards |
| 5,238,822 A | 8/1993 | Dykes |
| 5,597,895 A | 1/1997 | Gaynor |
| 5,606,026 A | 2/1997 | Rodman |
| 5,674,980 A | 10/1997 | Frankel |
| 5,891,994 A | 4/1999 | Goldstein |
| 6,193,981 B1 | 2/2001 | Goldstein |
| 6,399,067 B1 | 6/2002 | Goldstein |
| 6,524,582 B1 | 2/2003 | Goldstein |
| 6,525,179 B1 | 2/2003 | Goldstein |
| 2003/0166832 A1 | 9/2003 | Goldstein |
| 2003/0180326 A1 | 9/2003 | Goldstein |

FOREIGN PATENT DOCUMENTS

| | | |
|---|---|---|
| WO | WO87/02989 A1 | 5/1987 |
| WO | WO91/09958 A2 | 7/1991 |
| WO | WO91/10453 A1 | 7/1991 |
| WO | WO92/07871 A1 | 5/1992 |
| WO | WO92/14755 A1 | 9/1992 |
| WO | WO95/31999 A1 | 11/1995 |
| WO | WO99/02185 A1 | 1/1999 |

OTHER PUBLICATIONS

G. Zauli et al., "An Autocrine Loop of HIV Type–1 Tat Protein Responsible for the Improved Survival/Proliferation Capacity of Permanently Tat–Transfected Cells and Required for Optimal HIV–1 LTR Transactivating Activity", J. Acq. Imm. Def. Synd. Hum. Retrovirol., 10(3):306–316 (Nov. 1, 1995).

Webster's Ninth New Collegiate Dictionary, p. 602 (1990).

D. McPhee et al, "Recognition of Envelope and tat Protein Synthetic Peptide Analogs by HIV Positive Sera or Plasma", FEBS Letters, 233(2):393–396 (Jun., 1988).

C. Li et al, "Tat Protein Induces Self–Perpetuating Permissivity for Productive HIV–1 Infection", Proc. Natl. Acad. Sci. USA, 94:8116–8120 (Jul., 1997).

D. Brake et al, "Characterization of Murine Monoclonal Antibodies to the tat Protein from Human Immunodeficiency Virus Type 1", J. Virol., 64:962–965 (Feb., 1990).

Harlow et al, Antibodies, a Laboratory Manual, pp. 96–97 (1988).

J. Hinkula et al, "Recognition of Prominent Viral Epitopes Induced by Immunization with Human Immunodeficiency Virus Type 1 Regulatory Genes", J. Virol., 71(7):5528–5539 (Jul., 1997).

G. Pilkington et al, "Recombinant Human Fab Antibody Fragments to HIV–1 REV and TAT Regulatory Proteins: Direct Selection from a Combinatorial Phage Display Library", Mol. Immunol., 33(4/5):439–450 (1996).

M. Sande et al, "Antiretroviral Therapy for Adult HIV–Infected Patients", JAMA, 270(12):2583–2589 (Dec. 1, 1993).

M. Seligmann et al, "Concorde: MRC/ANRS Randomised Double–Blind Controlled Trial of Immediate and Deferred Zidovudine in Symptom–free HIV Infection", Lancet, 343:871–881 (Apr. 9, 1994).

L. Steinaa et al, "Antibody to HIV–1 Tat Protein Inhibits the Replication of Virus in Culture", Arch. Virol., 139:263–271 (1994).

K. Suzue et al, "Adjuvant–Free hsp70 Fusion Protein System Elicits Humoral and Cellular Immune Responses to HIV–1 p24", J. Immunol., 156:873–879 (Jan. 15, 1996).

(Continued)

*Primary Examiner*—James Housel  
*Assistant Examiner*—Jeffrey S. Parkin  
(74) *Attorney, Agent, or Firm*—Howson and Howson

(57) ABSTRACT

A composition which elicits antibodies to greater than 95%, and even greater than 99%, of the known variants of HIV-1 Tat protein contains at least one peptide or polypeptide of the formula of Epitope I (based on amino acids 2–10 of HIV-1 Tat consensus sequence) and optionally one or more of a peptide or polypeptide of Epitope II (based on amino acids 41 to 51 of that sequence), of Epitope III (based on amino acids 52–62 of that sequence), or of Epitope IV (based on amino acids 62 through 72 of that sequence with a C-terminal Pro). Vaccinal and pharmaceutical compositions can contain the antibodies induced by the peptide compositions for use in passive therapy. Diagnostic compositions and uses are described for assessing the immune status of vaccinated patients.

10 Claims, 4 Drawing Sheets

OTHER PUBLICATIONS

J. Tam, "Synthetic Peptide Vaccine Design: Synthesis and Properties of a High–Density Multiple Antigenic Peptide System", Proc. Natl. Acad. Sci. USA, 85:5409–5413 (Aug., 1988).

B. Tindall et al, "Primary HIV Infection: Host Responses and Intervention Strategies", AIDS, 5(1):1–14 (Jan., 1991).

S. Welles et al, "Prognostic Value of Plasma Human Immunodeficiency Virus Type 1(HIV–1) RNA Levels in Patients with Advanced HIV–1 Disease and with Little or No Prior Zidovudine Therap", J. Infect. Dis., 174:696–703 (Oct., 1996).

S. Wolinsky et al, "Adaptive Evolution of Human Immunodeficiency Virus–Type 1 During the Natural Course of Infection", Science, 272:537–542 (Apr. 26, 1996).

A. Meyerhans et al, "Temporal Fluctuations in HIV Quasispecies in vivo are not Reflected by Sequential HIV Isolations", Cell, 58:901–910 (Sep. 8, 1989).

J. Osborn, "The Rocky Road to an AIDS Vaccine", J. Acq. Imm. Def. Syndr. Hum. Retrovirol., 9(1):26–29 (May, 1995).

W. Paul, "Can the Immune Response Control HIV Infection?", Cell, 82:177–182 (Jul. 28, 1995).

B. Preston et al, "Fidelity of HIV–1 Reverse Transcriptase", Science, 242:1168–1171 (Nov. 25, 1988).

M. Re et al, "Effect of Antibody to HIV–1 Tat Protein on Viral Replication in Vitro and Progression of HIV–1 Disease in Vivo", J. Acq. Imm. Def. Synd. Hum. Retroviral., 10(4):408–416 (Dec. 1, 1995).

J. Roberts et al, "The Accuracy of Reverse Transcriptase from HIV–1", Science, 242:1171–1173 (Nov. 25, 1988).

M. Saag et al, "Hiv Viral Load Markers in Clinical Pratice", Nature Medicine, 2(6):625–629 (Jun., 1996).

M. Saag et al, "A Short–Term Clinical Evaluation of L–697, 661, a Non–Nucleoside Inhibitor of HIV–1 Reverse Transcriptase", N. Engl. J. Med., 329(15):1065–1072 (Oct. 7, 1993).

K. Saksela et al, "Human Immunodeficiency Virus Type 1 mRNA Expression in Peripheral Blood Cells Predicts Disease Progression Independently of the Numbers of CD4+ Lymphocytes", Proc. Natl. Acad. Sci. USA, 91:1104–1108 (Feb., 1994).

G. Goldstein, "HIV–1 Tat Protein is a Potential AIDS Vaccine", Nature Medicine, 2(9):960–964 (Sep., 1996).

B. Haynes, "Scientific and Social Issues of Human Immunodeficiency Virus Vaccine Development", Science, 260:1279–1286 (May 28, 1993).

W. Krone et al, "Natural Antibodies to HIV–tat Epitopes and Expression of HIV–1 Genes in Vivo", J. Med. Virol., 26:261–270 (Nov., 1988).

K. Kusumi et la, "Human Immunodeficiency Virus Type 1 Envelope Gene Structure and Diversity in vivo and after Cocultivation in vitro", J. Virol., 66(2):875–885 (Feb., 1992).

B. Larder et al, "HIV with Reduced Sensitivity to Zidovudine (AZT) Isolated During Prolonged Therapy", Science, 243:1731–1733 (Mar. 31, 1989).

T–H. Lee et al, "Circulating HIV–1–Infected Cell Burden from Seroconversion to AIDS: Importance of Postseroconversion Viral Load on Disease Course", J. Acq. Imm. Def. Synd., 7(4):381–388 (Apr., 1994).

N. Letvin, "Vaccines Against Human Immunodeficiency Virus—Progress and Prospects", N. Engl. J. Med., 329(19):1400–1405 (Nov. 4, 1993).

D. Mann et al, "Endocytosis and Targeting of Exogenous HIV–1 Tat Protein", EMBO J., 10(7):1733–1739 (Jul., 1991).

J. Mellors et al, "Prognosis in HIV–1 Infection Predicted by the Quantity of Virus in Plasma", Science, 272:1167–1170 (May 24, 1996).

A. Aldovini et al, "Synthesis of the Complete Trans–Activation Gene Product of Human T–Lymphotropic Virus Type III in *Escherichia coli*: Demonstration of Immunogenicity in vivo and Expression in vitro", Proc. Natl. Acad. Sci. USA, 83:6672–6676 (Sep., 1986).

C. Baumberger et al, "High Levels of Circulating RNA in Patients with Symptomatic HIV–1 Infection", AIDS, 7(Suppl. 2):S59–S64 (Nov., 1993).

M. Clerici et al, "T–Cell Proliferation to Subinfectious SIV Correlates with Lack of Infection after Challenge of Macaques", AIDS, 8(10):1391–1395 (Oct., 1994).

R. Coombs et al, "Association of Plasma Human Immunodeficiency Virus Type 1 RNA Level with Risk of Clinical Progression in Patients with Advanced Infection", J. Infect. Dis., 174:704–712 (Oct., 1996).

M. Daniel et al, "Protective Effects of a Live Attenuated SIV Vaccine with a Deletion in the nef Gene", Science, 258:1938–1941 (Dec. 18, 1992).

S. Fawell et al, "Tat–Mediated Delivery of Heterologous Proteins into Cells", Proc. Natl. Acad. Sci. USA, 91:664–668 (Jan., 1994).

A. Frankel et al, "Activity of Synthetic Peptides from the Tat Protein of Human Immunodeficiency Virus Type 1", Proc. Natl. Acad. Sci. USA, 86:7397–7401 (Oct., 1989).

```
         Sst I                    Bam HI
          |                         |
GAG CTC TAC AAA TCC GGG GAT CCG GGT GAA GAT CCG CGT TTA
Glu Leu Tyr Lys Ser Gly Asp Pro Gly Glu Asp Pro Arg Leu
 1               5                      10

Xma I
                     |
                     | Sma I
                     |  |
GAG CCG TGG AAA CAC CCG GGT TCT GGT TCT GTT GAC CCT AAC
Glu Pro Trp Lys His Pro Gly Ser Gly Ser Val Asp Pro Asn
15                      20                  25

BspM II
                                      |
CTT GAA CCT TGG AAG CAT CCT GGC AGC TCC GGA GTC GAT CCC
Leu Glu Pro Trp Lys His Pro Gly Ser Ser Gly Val Asp Pro
         30              35                  40

Xho I
      |
AAA CTC GAG CCC TGG AAA CAC CCC GGA AGT TCG GGG GTA GAC
Lys Leu Glu Pro Trp Lys His Pro Gly Ser Ser Gly Val Asp
             45              50                  55

Nco I                     PfiM I
               |                          |
CCA TCT CTG GAA CCA TGG AAG CAT CCA GGG AGT GGT AGC GTG
Pro Ser Leu Glu Pro Trp Lys His Pro Gly Ser Gly Ser Val
                 60              65                  70

Xma I
                               |
                               | Sma I
                               |  |
AAT CCG TCA TTA GAG CCG TGG AAA CAC CCG GGT TCA TCT GGA
Asn Pro Ser Leu Glu Pro Trp Lys His Pro Gly Ser Ser Gly
                     75              80

GTT GAT CCT CGC TTG GAA CCT TGG GAG CAT CCT GGT TCG TCC
Val Asp Pro Arg Leu Glu Pro Trp Glu His Pro Gly Ser Ser
             85              90              95

GGT GTA GAC CCC CGA CTT GAG CCC TGG AAT CAC CTC GGG AGT
Gly Val Asp Pro Arg Leu Glu Pro Trp Asn His Leu Gly Ser
         100             105                 110
```

FIGURE 2B

```
TCA GGC GTA GAT CAT CGG CTC GAA CCA TGG AAA CAT CCA GGT
Ser Gly Val Asp His Arg Leu Glu Pro Trp Lys His Pro Gly
        115                 120                 125

Alwn I
Nco I                   PfiM I Bgl II        OxaN I
|                       |      |             |
TCT GGA GAT CTG CGC CAG CGG CGA CGT ACT CCT CAG GAT TCT
Ser Gly Asp Leu Arg Gln Arg Arg Thr Pro Gln Asp Ser
        130                 135                 140

Nar I
            Tth I    |  Bbe I                    OxaN I
            |        |  |                        |
GGA TCT CGA CAA CGT CGG CGC CCT CCC CAA GAC TCC TCA GGA
Gly Ser Arg Gln Arg Arg Arg Pro Pro Gln Asp Ser Ser Gly
            145                 150

CGG CAG CGC CGA CGA CCC CCA CAG GGT TCA GGT TCA CGT CAA
Arg Gln Arg Arg Arg Pro Pro Gln Gly Ser Gly Ser Arg Gln
155                 160                 165

Tth I
    |
CGA CGC GGT CCA CCC CAA GGC TCG GGT TCG CGC CAG CGG CGA
Arg Arg Gly Pro Pro Gln Gly Ser Gly Ser Arg Gln Arg Arg
    170                 175                 180

Aat II                              Tth I
    |                                   |
CGT CCG CCT CAG AAC TCT AGT GGA CGA CAA CGT CGG CGC TCT
Arg Pro Pro Gln Asn Ser Ser Gly Arg Gln Arg Arg Arg Ser
        185                 190                 195

CCC CAA GAT TCC GGC GGG CGG CAG CGC CGT CGA TCA CCA CAG
Pro Gln Asp Ser Gly Gly Arg Gln Arg Arg Arg Ser Pro Gln
                200                 205                 210

AAC TCA GGT GGG CGT CAA CGA CGC CGG ACT CCG CAA TCT TCA Asn
Ser Gly Gly Arg Gln Arg Arg Arg Thr Pro Gln Ser Ser
                215                 220

Xma III
    |
TCC GGC CGC CAG CGG CGA CGT GCC CAT CAG AAT AGC GGC AGC
Ser Gly Arg Gln Arg Arg Arg Ala His Gln Asn Ser Gly Ser
225                 230                 235
```

FIGURE 2C

```
     Tth              BssH II
      |                |
CGA  CAA  CGT  CGG  CGC  GCA  CAC  CAA  GAC  AGC  AGT  GGG  CGG  CAG
Arg  Gln  Arg  Arg  Arg  Ala  His  Gln  Asp  Ser  Ser  Gly  Arg  Gln
     240                 245                      250

CGC  CGT  CGA  GCG  CCT  GAA  GAT  AGT  GGT  TCT  CGT  CAA  CGA  CGC
Arg  Arg  Arg  Ala  Pro  Glu  Asp  Ser  Gly  Ser  Arg  Gln  Arg  Arg
          255                      260                      265

BspMII                          ApaLI
                          |                               |
CGG  GCT  CCC  CCT  GAC  AGC  TCC  GGA  CGC  CAG  CGG  CAA  CGT  GCA
Arg  Ala  Pro  Pro  Asp  Ser  Ser  Gly  Arg  Gln  Arg  Gln  Arg  Ala
               270                      275                      280

OxaNI
           |
CCA  GAT  AGT  TCC  TCA  GGT  CAT  CAC  CAC  CAT  CAT  CAC  TAATAA
Pro  Asp  Ser  Ser  Ser  Gly  His  His  His  His  His  His
               285                      290

EcoR I  Bam HI  Xba I        Sal I    Hind III
 |       |       |             |        |
GAA  TTC  GGA  TCC  TCT  AGA  GTC  GAC  AAG  CTT
Glu  Phe  Gly  Ser  Ser  Arg  Val  Asp  Lys  Leu
          295
```

METHODS AND COMPOSITIONS FOR IMPAIRING MULTIPLICATION OF HIV-1

CROSS-REFERENCE TO OTHER INVENTIONS

This is a divisional of U.S. patent application Ser. No. 09/451,067, filed Nov. 30, 1999 now U.S. Pat. No. 6,525,179, which is a divisional of U.S. patent application Ser. No. 09/113,921, filed Jul. 10, 1998, now U.S. Pat. No. 6,193,981, issued Feb. 27, 2001, which is a continuation-in-part of U.S. patent application Ser. No. 08/893,853, filed Jul. 11, 1997, now U.S. Pat. No. 5,891,994, issued Apr. 6, 1999.

BACKGROUND OF THE INVENTION

The present invention relates generally to compositions and methods useful for inhibiting the multiplication of human immunodeficiency virus-1 (HIV-1) in infected patients, symptomatic or asymptomatic, and for attenuating HIV-1 multiplication during primary infection in previously uninfected subjects, thus minimizing progression to AIDS.

High plasma levels of human immunodeficiency virus type 1 (HIV-1) RNA are found during primary infection with HIV-1, the seroconversion illness, (C. Baumberger et al, AIDS, 7:(suppl 2): S59 (1993); M. S. Saag et al, Nature Med., 2:625 (1996)), after which they subside as the immune response controls the infection to a variable extent. Post seroconversion, lower but detectable levels of plasma HIV-1 RNA are present, and these levels rise with disease progression to again attain high levels at the AIDS stage (M. S. Saag et al, Nature Med., 2:265 (1996)). Approximately 50% of subjects have a symptomatic illness at seroconversion (B. Tindall and D. A. Cooper, AIDS, 5:1 (1991)) and symptomatic seroconversion is associated with an increased risk for the development of AIDS, probably because a severe primary illness is likely related to an early and extensive spread of HIV.

Inhibition of viral multiplication during the initial infection will likely reduce the subsequent development of chronic viremia leading to AIDS. Current medical practice, with administration of antiviral drugs for defined "at risk" situations, such as needle sticks with contaminated blood or pregnancy in HIV infected mothers, supports this concept.

Post seroconversion levels of HIV-1 RNA in plasma have proven to be the most powerful prognosticator of the likelihood of progression to AIDS (J. W. Mellors et al, Science, 272:1167 (1996); M. S. Saag et al, Nature Med., 2:265 (1996), R. W. Coomnbs et al, J. Inf. Dis., 174:704 (1996); S. L. Welles et al, J. Inf. Dis., 174:696 (1990)). Other measures of viral load, such as cellular RNA (K. Saksela et al, Proc. Natl. Acad. Sci. USA, 91:1104 (1994)) and cellular HIV proviral DNA (T-H. Lee et al, J. Acq. Imm. Def Syndromes, 7:381 (1994)) similarly establish the importance of the initial infection in establishing viral loads that determine future disease progression.

Thus, any intervention that inhibits HIV-1 infectivity during initial infection and/or lowers viral load post seroconversion is likely to have a favorable influence on the eventual outcome, delaying or preventing progression to AIDS.

A variety of methods are now employed to treat patients infected with human immunodeficiency virus (HIV-1), including treatment with certain combinations of protease inhibitor drugs. Unfortunately, however, this type of treatment is associated with serious side effects in some patients. Alternatively, vaccines are under development for control of the spread of HIV-1 to uninfected humans. However, this effort has largely been directed to proteins of the virus, expressed on the surface of infected cells, which are recognized by cytotoxic T cells with elimination of the infected cells, while free virus is blocked and cleared by antibody to surface antigens of the virion. Limitations of this mode of vaccination are readily apparent for HIV-1, which has demonstrated a great diversity in immunogenic viral epitopes and rapid mutational variations that occur within and between individuals (B. D. Preston et al., *Science*, 242:1168 (1988); J. D. Roberts et al., *Science*, 242:1171 (1988); A. R. Meyerhans et al., *Cell*, 58:901 (1989); K. Kusumi et al., *J. Virol.*, 66:875 (1992), B. A. Larder et al., *Science*, 243:1731 (1989); M. S. Sang et al., *N. Engl. J. Med.*, 329:1065 (1993); M. A. Sande, et al., *JAAM*, 270:2583 (1993); M. Seligmann et al., *Lancet*, 343:871 (1994); G. Meyers et al., *Human retroviruses and AIDS* 1993, *I-V. A compilation and analysis of nucleic acid and amino acid sequences*. Los Alamos National Laboratory, Los Alamos, N.Mex.)

Variation in strains of HIV-1 and frequent mutations of virion proteins have prevented successful application of conventional vaccine approaches (W. E. Paul, *Cell*, 82:177 (1995); J. E. Osborn, *J. Acq. Imm. Def. Syndr. Hum. Retrovirol.*, 9:26 (1995)). Mutation and selection of resistant variants is the central problem in developing a successful HIV-1 vaccine (M. D. Daniel et al., *Science*, 258:1938 (1992); N. L. Letvin, *N. Engl. J. Med*, 329:1400 (1993); M. Clerici et al., *AIDS*, 8:1391 (1994); S. M. Wolinsky et al, Science, 272:537 (1996)).

Other approaches to HIV-1 treatment have focused on the transactivating (tat) gene of HIV-1, which produces a protein (Tat) essential for transcription of the virus. The tat gene and its protein have been sequenced and examined for involvement in proposed treatments of HIV (see, e.g., U.S. Pat. No. 5,158,877, U.S. Pat. No. 5,238,882; U.S. Pat. No. 5,110,802; International Patent Publication No. WO92/07871, published May 14, 1992; International Patent Publication No. WO91/10453, published Jul. 25, 1991, International Patent Publication No. WO91/09958, published Jul. 11, 1991; International Patent Publication No. WO87/02989, published May 21, 1987). Tat protein is released extracellularly, making it available to be taken up by other infected cells to enhance transcription of HIV-1 in the cells and to be taken up by noninfected cells, altering host cell gene activations and rendering the cells susceptible to infection by the virus. Uptake of Tat by cells is very strong, and has been reported as mediated by a short basic sequence of the protein (S. Fawell et al., Proc. Natl. Acad. Sci., USA, 91:664–668 (1994)).

International Patent Publication No. WO92/14755, published Sep. 3, 1992, relates to the Tat protein and to the integrin cell surface receptor capable of binding to the Tat protein. Two Tat sequences that bind integrin are identified, which are the basic region or domain which is the dominant binding site for the integrin, having a peptide sequence of -Arg-Lys-Lys-Arg-Arg-Gln-Arg-Arg-Arg- (SEQ ID NO: 4), as well as -Gly-Arg-Gly-Asp-Ser-Pro- (SEQ ID NO: 5). This specification demonstrates that a number of peptides corresponding to these Tat sequences and the corresponding integrins block in vitro cell binding to Tat coated plates, as do antibodies to the appropriate integrins. However, the specification also shows that these reagents do not block uptake of functional Tat by cells (see Example 9 in WO92/14755), thus nullifying the proposed mechanism of action for therapeutic benefit in HIV infection. The Tat sequences described in this international application are distinct from the peptide immunogens of the present invention.

Both monoclonal and polygonal antibodies to Tat protein have been readily produced in animals and shown to block uptake of Tat protein in vitro (see, e.g., D. Brake et al, J. Virol., 64:962 (1990); D. Mann et al, EMBO J., 10:1733 (1991); J. Abraham et al, cited above; P. Auron et al, cited above; M. Jaye et al, cited above; G. Zauli et al, cited above). More recent reports showed that monoclonal or polyclonal antibodies to Tat protein added to tissue culture medium attenuated HIV-1 infection in vitro (L. Steinaa et al, Arch. Virol., 139:263 (1994); M. Re et al, J. Acq. Imm. Def. Syndr. Hum. Retrovirol., 10:408 (1995); and G. Zauli et al, J. Acq. Imm. Def. Syndr. Hum. Retrovirol., 10:306 (1995)).

The inventor's own publication (G. Goldstein, Nature Med., 2:960 (1996); see also, International Patent Publication No. WO95/31999, published Nov. 30, 1995) reviewed the evidence indicating that secretion of HIV-1 Tat protein from infected cells and uptake by both infected and uninfected cells was important for the infectivity of HIV-1. Previous studies also showed that antibodies to Tat protein in vitro blocked uptake of Tat and inhibited in vitro infectivity. Goldstein proposed active immunization of mammals to induce antibodies to HIV-1 Tat protein as a potential AIDS vaccine.

Despite the growing knowledge about HIV-1 disease progression, there remains a need in the art for the development of compositions and methods for treatment of HIV-1, both prophylactically and therapeutically, which are useful to lower the viral levels of HIV-1 for the treatment and possible prevention of the subsequent, generally fatal, AIDS disease.

SUMMARY OF THE INVENTION

In one aspect, the invention provides as a novel composition comprising a peptide or polypeptide, which comprises an amino acid sequence selected from the formula referred to as Epitope I: R1-Val-Asp-Pro-Y-Leu-Glu-Pro-R2 (SEQ ID NO: 36), wherein Y is variously Arg, Lys, Ser or Asn. The N-terminal R1 may represent hydrogen (i.e., the hydrogen on the unmodified N terminal amino acid), or a lower alkyl, or a lower alkanoyl. R1 may also include a sequence of between 1 to about 5 amino acids, optionally substituted with a lower alkyl or lower alkanoyl. In one embodiment, R1 is -X-Pro-, wherein X is Glu or Asp. Preferably, R1 represents 2 amino acids. The C-terminal R2 can also represent the hydroxyl group on the C terminal amino acid or an amide. To enhance titer R2 is preferably a sequence of between 1 to about 14 additional amino acids amidated at the carboxyl terminus. In a preferred embodiment, R2 is -Trp-Lys-His-Pro-Gly-Ser- amide (SEQ ID NO: 10). The peptides or polypeptides of these compositions arereproduced synthetically or recombinantly. This composition may take the form of one or more of the above-described peptides expressed as a synthetic peptide coupled to a carrier, or expressed as a multiple antigenic peptide, or the selected peptides may be expressed within a recombinantly produced protein. This composition is designed to induce antibodies reactive with greater than 95% of the known variants of the HIV-1 Tat protein.

In another aspect, the above-described composition further contains lone or more additional peptide or polypeptide(s) which represent other amino acid sequences which correspond to amino acid residues 2 or 4 to 10 of an HIV-1 Tat protein. These optional amino acid sequences are described in detail below. These sequences are preferably from an HIV-1 strain with a Tat protein variant at that location.

In another aspect, the invention provides a novel composition comprising a peptide or polypeptide of the formula referred to as Epitope II: R3-Lys-X-Leu-Gly-Ile-Ser-Tyr-Gly Arg-Lys-Lys-R4 (SEQ ID NO: 37). According to this formula, X is Gly or Ala. The N termninal R3 may represent hydrogen (i.e., the hydrogen on the unmodified N terminal amino acid), or may be a lower alkyl or a lower alkanoyl. R3 may also include a sequence of between 1 to about 5 amino acids, optionally substituted with a lower alkyl or lower alkanoyl. The C terminal R4 may be the free hydroxyl of the C terminal amino acid, or an amide, or a sequence of one or up to about 5 additional amino acids, optionally substituted with an amide. The peptides or polypeptides of these compositions are produced synthetically or recombinantly, provided that the recombinant Epitope II peptide is situated at the C terminus of the recombinant protein. This composition may take the form of one or more of the above-described peptides expressed as a synthetic peptide coupled to a carrier, or expressed as a multiple antigenic peptide. This composition is designed to induce antibodies reactive with greater than about 95% of the known variants of HIV-1 Tat protein.

In yet a further aspect, this invention provides a composition comprising a peptide or polypeptide of the formula referred to as Epitope III: R5-Arg-Arg-X-Z-A-Y-Ser-R6 (SEQ ID NO: 38), wherein X is selected from the group consisting of Ala, Pro, Ser and Gin; wherein Y is selected from the group consisting of Asp, Asn, Gly and Ser; wherein Z is selected from the group consisting of Pro and His; and wherein A is selected from the group consisting of Gin and Pro. The N terminal R5 is hydrogen, a lower alkyl, a lower alkanoyl, or a sequence of between 1 to about 3 amino acids, optionally substituted with a lower alkyl or lower alkanoyl. In a preferred embodiment R5 is -Gln-Arg-, optionally modified as above. The C terminal R6 is either a free hydroxyl or an amide. A preferred embodiment of such a composition contains at least three Epitope ID peptides, i.e., -Gln-Arg-Arg-Arg-Ala-Pro-Gln-Asp-Ser- (amino acids 54–62 of SEQ ID NO: 1), -Gln-Arg-Arg-Arg-Ala-His-Gln-Asp-Ser- (amino acids 2–10 of SEQ ID NO: 65), and -Gln-Arg-Arg-Arg-Ala-Pro-Pro-Asp-Ser- (amino acids 264–272 of SEQ ID NO: 3), optionally modified as above. Other peptides or polypeptides representative of amino acids 56–62 of Tat, but having different sequences from that of the above formula may also be included in the composition. The peptides or polypeptides of these compositions are produced synthetically or recombinantly. This composition may take the form of one or more of the above-described peptides expressed as a synthetic peptide coupled to a carrier, or expressed as a multiple antigenic peptide, or the selected peptides may be expressed within a recombinantly produced protein. This composition is designed to induce antibodies reactive with greater than about 75% of all known variants of HIV-1 Tat protein.

In still a further aspect, this invention provides a composition comprising a peptide or polypeptide of the formula referred to as Epitope IV: R7-Ser-Gln-X-His-Gln-Y-Ser-Leu-Ser-Lys-Gln-Pro-R8 (SEQ ID NO: 39), wherein X is selected from the group consisting of Asn and Thr; and wherein Y is selected from the group consisting of Ala and Val. The N terminal R7 may be hydrogen, a lower alkyl, a lower alkanoyl, or a sequence of between 1 to about 3 amino acids, optionally substituted with a lower alkyl or lower alkanoyl. The C terminal R8 may be a free hydroxyl, an amide, or a sequence of one or up to about 3 additional amino acids, optionally substituted with an amide. A preferred Epitope IV peptide is -Ser-Gln-Thr-His-Gln-Ala-Ser-Leu-Ser-Lys-Gln-Pro- (SEQ ID NO: 40). The peptides or polypeptides of these compositions are produced synthetically or recombinantly. This composition may take the form of one or more of the above-described peptides expressed as a synthetic peptide coupled to a carrier, or expressed as a multiple antigenic peptide, or the selected peptides may be expressed within a recombinantly produced protein. This composition is designed to induce antibodies reactive with greater than 64% of all known variants of HIV-1 Tat protein.

In still another aspect, this invention provides composition described above that contains peptides or polypeptides which comprise one or more Epitope I peptides in combination with one or more Epitope It peptides, and/or one or more Epitope III peptides, and/or one or more Epitope IV peptides. Such compositions can combine appropriate Epitope peptides, so as to provide for a composition than induces antibodies reactive with greater than about 99% of all known HIV-1 Tat proteins.

In yet a further aspect, the invention provides a synthetic gene which encodes sequentially a peptide or polypeptide that contains at least one Epitope I amino acid sequence defined above, optionally with a carboxy terminal Epitope II peptide, or contains at least two Epitope I amino acid sequences. The synthetic gene may contain each amino acid sequence separated by a spacer sequence, or may express each peptide/polypeptide in an open reading frame with a carrier protein. The synthetic gene may be separated from the carrier protein by a spacer if the spacer is fused to an Epitope I sequence, leaving an Epitope II sequence at the carboxy terminus of the recombinant protein. Further embodiments include multiple Epitope I peptides fused together and to the carrier protein.

In yet a further aspect, the invention provides a synthetic molecule, e.g., a vector, comprising the above-described synthetic gene, operatively linked to regulatory nucleic acid sequences, which direct and control expression of the product of the synthetic gene in a host cell.

In another aspect, the invention provides a recombinant virus which contains the above described synthetic gene or synthetic molecule, which virus is capable of expressing multiple copies of the product of the gene or molecule in a host cell. The virus is non-pathogenic to humans.

In yet another aspect, the invention provides a commensal bacterium which contains the above described synthetic gene or synthetic molecule, which bacterium is capable of expressing multiple copies of the product of the gene or molecule and inducing antibodies in a mammalian host.

In still a further aspect, the invention provides an isolated antibody composition which is directed against a peptide or polypeptide of the compositions described above. Antibodies may also be obtained against multiple components of the compositions described above. This antibody is produced by immunizing a mammal with a peptide/polypeptide composition of the invention, a synthetic gene or synthetic molecule of the invention; a recombinant virus or commensal bacterium of the invention; and isolating and purifying antibody from said immunized mammal. Alternatively, the antibody may be a polyclonal antibody, a monoclonal antibody, a chimeric antibody, a humanized antibody, a human antibody, or mixtures thereof.

Thus, another aspect of the invention is a pharmaceutical composition useful for inducing antibodies that react with greater than 95%, and preferably greater than 99%, of the known HIV-1 Tat proteins. These induced antibodies can impair the multiplication of HIV-1. The pharmaceutical composition comprises at least one of the recombinant or synthetic peptide/polypeptide compositions described above; the synthetic gene/molecule described above; the recombinant virus described herein, or the commensal bacterium described herein, in a pharmaceutically acceptable carrier.

Still a further aspect of the invention is a pharmaceutical composition useful for impairing the multiplication of HIV-1, this composition containing an above described antibody composition.

In yet a further aspect of the invention, a method for reducing the viral levels of HIV-1 involves exposing a human to antibody-inducing pharmaceutical compositions described above, actively inducing antibodies that react with most HIV-1 Tat proteins, and impairing the multiplication of the virus in vivo. This method is appropriate for an HIV-1 infected subject with a competent immune system, or an uninfected or recently infected subject. The method induces antibodies which react with HIV-1 Tat proteins, which antibodies reduce viral multiplication during any initial acute infection with HIV-1 and minimize chronic viremia which leads to AIDS.

In still another aspect, the invention provides a method for reducing the viral levels of HIV-1 by administering to a human, who is incapable of mounting an effective or rapid immune response to infection with HIV-1, a pharmaceutical composition containing the antibody compositions described above. The method can involve chronically administering the composition.

Yet other aspects of the invention include methods for producing the compositions described above, as well as host cells transfected with such compositions.

Still another aspect of this invention is a kit useful for the measurement and detection of titers and specificities of antibodies induced by vaccination with the compositions described above. The kit of the invention includes peptides of Epitopes I through IV, and coated solid supports, a labelled reagent for detecting the binding of antibodies to these peptides, and miscellaneous substrates and apparatus for evoking or detecting the signals provided by the labels, as well as conventional apparatus for taking blood samples, appropriate vials and other diagnostic assay components.

In yet a further aspect, the invention provides a method for detecting the titers and reactivity patterns of antibodies in subjects vaccinated with the compositions of this invention. The method includes the steps of incubating dilutions of the subject's biological fluid, e.g. serum, with plates or beads on which are bound one or more peptides of the Epitopes I through IV, washing away unbound biological materials, and measuring any antibody binding to the peptides with labeled reagent, e.g., an anti-human immunoglobulin to which is associated an enzyme. Depending on the type of label employed, the signal produced by the label may be evoked by further adding a substrate which reacts with the enzyme, e.g., producing a color change. Other conventional labels may also be incorporated into this assay design.

Other aspects and advantages of the present invention are described further in the following detailed description of the preferred embodiments thereof.

BRIEF DESCRIPTION OF THE DRAWINGS

FIG. 1 illustrates an HIV-1 Tat protein consensus sequence (SEQ ID NO: 1), based on Tat protein sequences of 31 known HIV-1 strains found in the common B subtype (NIH Los Alamos database). The amino acid positions in which variations appear are in lower case letters.

FIGS. 2A–2C illustrate a synthetic gene which encodes a fusion protein (SEQ ID NO: 3) of this invention, described in detail in Example 5 below.

DETAILED DESCRIPTION OF THE INVENTION

The present invention provides a solution to the above-stated problem by providing compositions which induce antibodies in uninfected or early stage infected subjects still capable of mounting an immune response to an immunogen, the antibodies reacting with greater than 95%, and preferably, greater than 99% of known HIV-1 Tat protein variants. The induced antibodies can inhibit multiplication of HIV-1. This prevents further disease progression to AIDS. Antibody compositions are also provided for use in infected or non-infected humans, who are incapable of mounting an effective or rapid immune response to HIV-1 infection. These compositions are capable of reacting with greater than 95%, and preferably greater than 99%, Tat proteins thus reducing viral levels of HIV-1. These antibodies are useful in both therapeutic and prophylactic contexts to control the development of AIDS in a large population exposed to, or infected by, HIV-1 strains which produce upon infection immunologically distinct Tat proteins.

The compositions of the present invention, which are based on peptides provided by certain epitopes of HIV-1 Tat protein, may be proteinaceous in nature, or may be nucleic acid compositions which encode the peptides and polypeptides that induce antibodies to Tat, which in turn impair multiplication of HIV-1.

Figure 1:
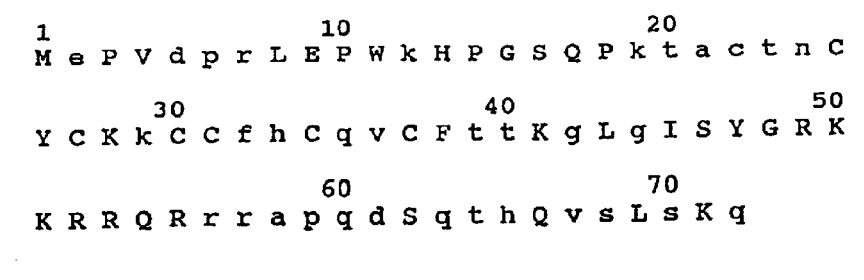

HIV-1 Tat protein is produced from two exons: Exon 1 encodes a 72 amino acid (aa) protein (see FIG. 1, SEQ ID NO: 1) which may be expressed without splicing or be spliced with the approximately 29 amino acid peptide encoded by Exon 2 to produce an approximately 101 amino acid peptide. Since the 72 amino acid product of Exon 1 is capable alone of cellular uptake and activation, it is essential that antibodies react with and interdict intercellular transport of the 72 amino acid peptide. HIV-1 Tat contains Cys at aa positions 22 and 37 of Exon 1 (SEQ ID NOS: 1 and 2), and 5 additional Cys between these. This region of the peptide is termed the Cys rich region and has Cys-Cys covalent linkages producing complex tertiary structure. The scientific literature has indicated that this region does not appear to be immunogenic. The inventor has identified epitopes, i.e., binding regions, recognized by antibodies (antigenic sequences) in the N-terminal linear sequence 1–21 (22 aa) and the C-terminal linear sequence 38–72 (35 aa) of Exon 1 (SEQ ID NO: 2) or other Tat sequence variants. Immunogenic regions of these larger sequences were identified by the inventor and are underlined in the N terminal and C terminal consensus sequences of Exon 1 below: Epitope I was identified as the nine amino acid sequence of aa positions 2–10 of Exon 1. Epitope II was identified as the eleven amino acid sequence of aa positions 41–51 of Exon 1. Epitope III was identified as the 7 amino acid sequence of aa positions 56–62 of Exon 1. Epitope IV was identified as the twelve amino acid sequence of aa positions 62–73 of Tat, including the the first Pro (aa 73) of Exon 2 and overlaps Ser 62 of Epitope III (dotted underlining).

The term "Tat sequence variant" means a polypeptide or peptide containing Tat protein amino acid residues, or a sequence from another HIV-1 strain Tat protein that is substantially similar to the sequence of SEQ ID NO: 1. Each variant may differ from the consensus sequence of FIG. 1 (SEQ ID NO: 1) and/or from another variant by at least one amino acid change within the residues of interest for Epitopes I through IV. This change may provide the same or different antigenic specificity to that particular Tat Epitope when added to the composition of the invention.

A. Epitope I Immunogenic Compositions

Therefore, in one embodiment, the present invention provides a composition containing a non-naturally occurring peptide or polypeptide, which comprises one or more Epitope I amino acid sequences. These Epitope I sequences elicit a specific humoral immune response (for the purpose of this invention) in a mammal exposed to the Epitope I sequences in vivo. The Epitope I amino acid sequences correspond to amino acid residues 2–10 or 4–10 of the Tat consensus sequence (SEQ ID NO: 1) of FIG. 1 which is derived from a number of "Tat sequence variants".

Epitope I defines peptides of the general formula: R1-Val-Asp-Pro-Y-Leu-Glu-Pro-R2 (SEQ ID NO: 36). The N-terminal R1 may represent the hydrogen on the unmodified N terminal amino acid Val, or R1 may be a lower alkyl, or a lower alkanoyl attached to the Val. R1 may also include a sequence of between 1 to about 5 amino acids, optionally substituted with a lower alkyl or lower alkanoyl. In one embodiment, R1 is -X-Pro-, wherein X is Glu or Asp. The C-terminal R2 can represent the hydroxyl group on the C terminal amino acid Pro, or R2 can be an amide on the Pro; alternatively, R2 is a sequence of between 1 to about 14 additional amino acids, optionally amidated at the carboxyl terminus. The X and Y positions represent common variants of this Epitope peptide, wherein X is Glu (90%) or Asp (10%), and Y is variously Arg (74%), Lys (11%), Ser (9%) or Asn (4%). Peptides containing Glu or Asp at position X induce antibodies that effectively cross-react with the other variant. Alternatively, peptides omitting the X-P effectively induce antibodies to Val-Asp-Pro-Arg-Leu-Glu-Pro (amino acids 4–10 of SEQ ID NO: 1). A desirable immunogen of the formula Glu-Pro-Val-Asp-Pro-Lys-Leu-Glu-Pro (SEQ ID NO: 56) reacts/cross-reacts with greater than 95% of known HIV-1 Tat proteins, while an immunogen of the formula Val-Asp-Pro-Lys-Leu-Gly-Pro (SEQ ID NO: 57) reacts/cross-reacts with greater than 97% of known HIV-1 Tat proteins.

Antibodies to all four position Y variants are generated by using all four as immunogens. Alternatively, cross-reactivity permits a reduction to two or even one immunizing sequence to induce reactivity to all four position Y variants. As discussed in detail in the Examples below, the reactivities of antibodies induced by the Epitope I-containing peptide: Val-Asp-Pro-Y-Leu-Glu-Pro-Typ-Lys-His-Pro-Gly-Ser- (SEQ ID NO: 58), where Y is Arg, Lys, Ser or Asn, are

```
                                                                    (SEQ ID NO: 54)
 1                                                               21
Met Glu Pro Val Asp Pro Arg Leu Glu Pro Trp Lys His Pro Gly Ser Gln Pro Lys Thr Ala
                                                                    (SEQ ID NO: 55)
38           41                                     51          56
Phe Ile Thr Lys Gly Leu Gly Ile Ser Tyr Gly Arg Lys Lys Arg Arg Gln Arg Arg Arg Ala
            62                                  72
Pro Gln Asp Ser Gln Thr His Gln Val Ser Leu Ser Lys Gln Pro.
------------------------------------------------
``` reported in Table 1 below. Dark shading shows self-reactivity, pale shading shows significant (40%) cross-reactivity.

TABLE 1

| Immunizing Peptides | Detector Peptides (GMT (% self-binding)) | | | |
|---|---|---|---|---|
| Position Y | Arg | Lys | Ser | Asn |
| Arg | ▓▓▓ | 10,000 (13) | 10,000 (13) | 9,000 (12) |
| Lys* | 31,000 (62) | ▓▓▓ | 35,000 (43) | 45,000 (65) |
| Ser | 8,000 (6) | 8,000 (6) | ▓▓▓ | 14,000 (11) |
| Asn* | 17,000 (13) | 12,000 (9) | 61,000 (46) | ▓▓▓ |

*Only one high titer antiserum available.

Preferably a composition of this invention contains one or more the following Epitope I peptides or polypeptides:

R1-Val-Asp-Pro-Arg-Leu-Glu-Pro-R2 (SEQ ID NO: 6);
R1-Val-Asp-Pro-Lys-Leu-Glu-Pro-R2 (SEQ ID NO: 7);
R1-Val-Asp-Pro-Ser-Leu-Glu-Pro-R2 (SEQ ID NO: 8);
R1-Val-Asp-Pro-Asn-Leu-Glu-Pro-R2 (SEQ ID NO: 9).

As demonstrated above, the immunogen in which Y is Lys (SEQ ID NO: 7) induces antibodies with good reactivity with the three other variants. No immunogen induced high titer antibodies with good cross-reactivity with the variant in which Y was Ser. Thus an immunogen of Epitope I in which Y was Lys (SEQ ID NO: 7) may suffice for full cross-reactivity to all four position Y variants, and may be used alone in an immunogenic composition. While this pattern of response of the peptide in which Y is Lys occurs in the majority of tests to date, it should be expected by one of skill in the art, that some differences in cross-reactivity from the results above may occur in some test samples.

Alternatively, compositions of this invention comprise two, three or all four of these amino acid sequences (SEQ ID NOS: 6–9). Alternatively, a combination of Epitope I immunogens in which Y was Lys and in which Y was Asn (SEQ ID NO: 6) should provide somewhat better titers for Epitope I variants in which Y was Ser or Y was Asn.

Still another alternative Epitope I peptide immunogen contains at position Y an ornithine, since the ornithine side chain is similar to lysine with one less -$CH_2$-. This Epitope I sequence may provide even more cross-reactivity, and may be used alone or in combination with other Epitope I immunogens.

According to the formula of Epitope I above, the seven amino acid residues which form the minimum reactive Epitope I sequences, may be flanked by other amino acids, so that the entire Epitope I sequence may be between 7 and about 25 amino acids in length. As indicated in Example 1 below, the identity of the flanking amino acids is not essential to the biological function of the Epitope I immunogen. In particular additional amino acids on the N-terminus of Epitope I sequences do not affect immunogenicity. Thus, the N-terminal R1 of Epitope I may be selected from the group consisting of a free N terminal amino acid hydrogen, a lower alkyl (i.e., C1–C10 alkyl), a lower C1–C10 alkanoyl, such as an acetyl group, or a sequence of between 1 to about 5 amino acids. Preferably, R1 represents 2 amino acids.

Additional amino acids on the C-terminus of the Epitope I minimum sequence enhance antibody titer. Epitope I immunogens require at least two amino acid extensions at the C-terminus for optimal immunogenicity and are immunogenic when present within extended amino acid sequence. Thus, while the C-terminal R2 can be a simple free hydroxyl group, it can also be a C terminal amide. However, to enhance titer, R2 is preferably a sequence of between 1 to about 14 additional amino acids amidated at the carboxyl terminus. In a preferred embodiment, R2 is -Trp-Lys-His-Pro-Gly-Ser-amide (SEQ ID NO: 10).

The above-described Epitope I composition of the invention may contain a number of additional peptides or polypeptides, which contain other sequences which correspond to amino acid residues between aa 2-aa10 of SEQ ID NO: 1, but are derived from other Tat variants which do not cross-react well with antibodies to the Epitope I compositions described above. These additional peptides and polypeptides are referred to as "optional Epitope Ia immunogens". For example, optional Epitope Ia immunogens which can be present in compositions of this invention, can contain at least one copy of at least one of the following amino acid sequences (SEQ ID NOS: 11 through 18, respectively):

R1-Gly-Pro-Arg-Leu-Glu-Pro-R2;
R1-Ala-Pro-Arg-Leu-Glu-Pro-R2;
R1-His-Pro-Arg-Leu-Glu-Pro-R2;
R1-Asp-Pro-Gly-Leu-Glu-Pro-R2;
R1-Asp-Pro-Arg-Ile-Glu-Pro-R2;
R1-Asp-Pro-Arg-Leu-Gly-Pro-R2;
R1-Asp-Pro-Arg-Leu-Glu-Ala-R2; and
R1-Asn-Pro-Ser-Leu-Glu-Pro-R2.

The Epitope I compositions of this invention may contain multiple copies of a single peptide, or multiple copies of different Epitope I peptides, including optionally Epitope Ia peptides, in any order, or multiple copies of at least two of these peptides. In one embodiment, at least one copy of all four amino acid sequences (SEQ ID NOS: 6–9) are present.

As described in more detail below, the Epitope I and Ia peptides or polypeptides of these compositions are produced synthetically or recombinantly. The Epitope I immunogens can be expressed as synthetic peptides coupled to a carrier protein. The Epitope I immunogens may also be expressed as multiple antigenic peptides, optionally coupled to a carrier protein. Alternatively, the Epitope I immunogens may be expressed within recombinantly produced protein, optionally co-expressed or fused in frame with a carrier protein.

Epitope I compositions demonstrate a biological activity of inducing in an immunized, immune competent mammal, i.e., a non-infected human, or an asymptomatic infected human, an active humoral immune response (i.e., antibodies) that is directed against greater than 95%, and preferably greater than 99%, of the known variants of Tat proteins of HIV-1. The end result of such treatment is an impairment of the multiplication of HIV-1 in an acute infection, thereby preventing high post-seroconversion plasma levels of HIV-1 that are associated with progression to AIDS. Active induction of antibodies in the early asymptomatic phase of HIV infection may reduce viral multiplication, lower the plasma viral load and reduce the likelihood of progression to AIDS. The composition which contains at least one Epitope I immunogen up to all four of the SEQ ID NO: 6–9 amino acid sequences, can elicit an immune response to about 97% of the 400 known Tat sequences of the common B subtypes of HIV-1 and with Tat proteins of all 18 non-B subtype HIV-1 that have been sequenced (courtesy of Dr. Esther Guzman, Los Alamos NLAID HIV database, GenBank database).

B. Epitope II Immunogenic Compositions

In another embodiment, the present invention provides a composition comprising at least one Epitope II amino acid sequence. This Epitope II sequence elicits a specific humoral immune response (for the purpose of this invention) in a mammal exposed to the Epitope II sequence in vivo. Epitope II defines peptides of the formula R3-Lys-X-Leu-Gly-Ile-Ser-Tyr-Gly-Arg-Lys-Lys-R4, wherein X is Gly (70%) or Ala (30%). This sequence is highly conserved. The immunogen in which X is Gly induces antibodies cross-reactive with the sequence in which X is Ala.

The N terminal R3 may represent the hydrogen on the unmodified N terminal amino acid Lys, or R3 may be a lower alkyl, or a lower alkanoyl, such as an acetyl group, substituent on the Lys. R3 may also include a sequence of between 1 to about 5 amino acids, optionally substituted with a lower alkyl or lower alkanoyl. The C terminal R4 may represent the free hydroxyl of the C terminal amino acid Lys, or R4 may be an amide on that C terminal amino acid. R4 may optionally be a sequence of one or up to about 5 additional amino acids, optionally substituted with an amide. The presently preferred immunogen for Epitope II is -Lys-Gly-Leu-Gly-Ile-Ser-Tyr-Gly-Arg-Lys-Lys- (amino acids 41–51 of SEQ ID NO: 1). This would react/cross-react with greater than 96% of known HIV-1 Tat proteins.

Epitope II is poorly immunogenic when presented within other sequences. Thus, for optimal immunogenicity, this sequence is prepared as a synthetic peptide fused to, or coupled to, a carrier protein or as a multiple antigenic peptide, optionally coupled to carrier protein. Alternatively, Epitope II may be expressed as the C terminal sequence of a recombinant protein, which is optionally fused in frame to a carrier protein at its amino terminal sequence. In a composition of this invention, an Epitope II peptide is preferably presented alone or in combination with one or more Epitope I peptides. Other compositions may employ one or more Epitope III or IV peptides.

C. Epitope III Immunogenic Compositions

In another embodiment, the present invention provides a composition comprising at least one, and preferably two or more Epitope III amino acid sequences. These Epitope III sequences elicit a specific humoral immune response (for the purpose of this invention) in a mammal exposed to the Epitope III sequences in vivo. This epitope shows considerable more variation than Epitopes I and II. These Epitope III immunogenic peptides and polypeptides are derived from Tat variant protein sequences corresponding to amino acids 56–62 of SEQ ID NO: 1. Epitope III defines peptides of the formula: R5-Arg-Arg-X-Z-A-Y-Ser-R6 (SEQ ID NO: 38), wherein X may be Ala, Pro, Ser or Gln; Y may be Asp, Asn, Gly or Ser; Z may be Pro or His; and A may be Gln or Pro. The Epitope III immunogens in which X is Ala induce antibodies that cross-react with the other position X variants. Epitope III immunogens containing Asp in position Y induce antibodies that cross-react with the other position Y variants. The three most common variants for positions Z and A are -Pro-Gln- (61%), -Pro-Pro- (8%) and -His-Gln- (8%). Antibodies induced by these three immunogens do not cross-react with the others so that three immunogens would need to be used to cover these variants (77%).

According to the formula of Epitope III above, the seven amino residues which form the minimum reactive Epitope III sequences, may be flanked by other amino acids, so that the entire Epitope III sequence may be between 7 and about 15 amino acids in length. As indicated in Example 3 below, the identity of the flanking amino acids is not essential to the biological function of the Epitope III immunogen. In particular additional amino acids on the N-terminus of Epitope III sequences do not affect immunogenicity. The N terminal R5 may optionally represent the hydrogen on the N-terminal Arg, or R5 is a lower alkyl or alkanoyl, such as an acetyl group, substituent on the N-terminal Arg. Alternatively, R5 is a sequence of between 1 to about 3 amino acids, optionally substituted with a lower alkyl or lower alkanoyl. In a preferred embodiment R5 is -Gln-Arg-, optionally modified as above, which improves the immunogenicity of the Epitope. The C terminal R6 represents either the free hydroxyl on the C terminal amino acid or an amide substituent on the C terminal amino acid, because any C-terminal extension impairs immunogenicity.

Epitope III immunogens which can be present in compositions of this invention can include at least one copy of at least one of the following preferred Epitope III amino acid sequences: R5-Gln-Arg-Arg-Arg-Ala-Pro-Gln-Asp-Ser-R6, R5-Gln-Arg-Arg-Arg-Ala-His-Gln-Asp-Ser-R6, and R5-Gln-Arg-Arg-Arg-Ala-Pro-Pro-Asp-Ser-R6, optionally modified as above (SEQ ID NOS: 20 through 22, respectively).

Still other optional immunogenic sequences which may be included in the Epitope III compositions include R5-Arg-Arg-Pro-Pro-Gln-Asp-Asn-R6, R5-Arg-Arg-Ala-Pro-Gln-Asp-Arg-R6, R5-Arg-Gly-Ala-Pro-Gln-Asp-Ser-R6; R5-Arg-Arg-Ala-Pro-Glu-Asp-Ser-R6; or R5-Arg-Arg-Ala-Ser-Gln-Asp-Ser-R6 (SEQ ID NOS: 23 through 27, respectively). As can be determined from review of the examples below, the inclusion of these Epitope III peptides in compositions of the invention can induce antibodies that react with rare Tat proteins of HIV-1 which are not cross-reactive with, or do not have a sufficiently strong cross-reactivity to, antibodies induced by the preferred Epitope III immunogens.

As described in more detail below, the Epitope III peptides or polypeptides are poorly immunogenic when presented within other sequences. Although the Epitope III sequences may be prepared recombinantly, for optimal immunogenicity, these sequences would be prepared synthetically and coupled to a carrier protein, or as multiple antigenic peptides, optionally coupled to carrier protein. Alternatively, Epitope III may be expressed as the C terminal sequence of a recombinant protein, which is optionally fused in frame to a carrier protein at its amino terminal sequence. Compositions of this invention would preferably contain three or more different Epitope III immunogens, optionally with at least one Epitope I immunogen, and optionally with one or more Epitope II or Epitope IV immunogens.

D. Epitope IV Immunogenic Compositions

In another embodiment, the present invention provides a composition comprising at least one, and preferably two or more Epitope IV amino acid sequences. These Epitope IV sequences elicit a specific humoral immune response (for the purpose of this invention) in a mammal exposed to the Epitope IV sequences in vivo. The Epitope IV immunogenic peptides and polypeptides are derived from Tat variant protein sequences corresponding to amino acids 62–72 of SEQ if) NO: 1, including a C-terminal Pro from Exon 2 of HIV-1 Tat. Epitope IV defines peptides of the formula: R7-Ser-Gln-X-His-Gln-Y-Ser-Leu-Ser-Lys-Gln-Pro-R8 (SEQ ID NO: 39), wherein X may be Asn or Thr; and Y may be Ala or Val. The immunogen in which X is Thr induces antibodies that cross-react with the immunogen in which X is Asn. The immunogen in which Y is Val induce antibodies that do not cross-react with the peptides in which Y is Ala. However, the peptides containing Ala in position Y induce antibodies that cross-react with peptides for Epitope IV in which Y is Val. Thus the optimal Epitope IV immunogen is Ser-Gln-Thr-His-Gln-Ala-Ser-Leu-Ser Lys-Gln-Pro (SEQ ID NO: 40) and this induces antibodies reactive/cross-reactive with 64% of known HIV-1 Tat proteins.

According to the formula of Epitope IV above, the twelve amino residues which form the minimum reactive Epitope IV sequences, may be flanked by a few other amino acids, so that the entire Epitope IV sequence may be between 12 and about 18 amino acids in length. The N terminal R7 may represent the hydrogen of the N terminal amino acid, or a lower alkyl or alkanoyl, such as an acetyl group, substituent on the N terminal amino acid. Although N-terminal extension markedly inhibits immunogenicity, the R7 may also be a sequence of between 1 to about 3 amino acids, optionally substituted with a lower alkyl or lower alkanoyl. The C terminal R8 may represent the free hydroxyl on the C terminal amino acid, or an amide substituent on the C terminal amino acid, or R8 may be a sequence of one or up to about 3 additional amino acids, optionally substituted with an amide. Additionally, the C-terminal Pro, which is an important component of the epitope, is encoded by Exon 2 of Tat. Thus antibodies to Epitope IV would be poorly reactive with non-spliced Tat Exon 1 protein.

This Epitope IV sequence is poorly immunogenic when presented within other sequences, Thus, for optimal immunogenicity, this sequence would be prepared as a synthetic peptide coupled to carrier protein or as a multiple antigenic peptide, optionally coupled to carrier protein. Compositions of this invention would preferably contain two or more different Epitope IV immunogens, optionally with at least one Epitope I immunogen, and optionally with one or more Epitope II or Epitope III immunogens.

E. Compositions Containing Multiple Epitopes

While the amino acid sequences of Epitope I, II, III and IV and optional immunogens identified herein were obtained by rigorous analysis of over 400 known Tat sequences of HIV-1, it should be understood by one of skill in the art that similar compositions may be obtained, following the teachings of this invention, from the study of further Tat proteins, the nucleic acid sequences encoding them, and fragments thereof from newly isolated Tat proteins of HIV-1 subtype B, or from Tat proteins of the other subtypes, or from other HIV strains.

Thus, the compositions of this invention, i.e., the peptide/polypeptides containing the above-identified amino acid sequences, when provided to a human subject, are useful in the immunologic interdiction of extracellular Tat proteins of most HIV-1 strains. These compositions function to critically reduce explosive multiplication of the virus and permit effective immune control of the virus.

The immunogens for each Epitope are preferably designed to induce antibodies reactive with the highest proportion of naturally occurring variants of each epitope. For an epitope such as Epitope I, multiple copies of an immunogen could be incorporated in a synthetic or recombinant immunogen to enhance the immunogenicity and produce higher titer antibodies. Furthermore, immunogens for two or more epitopes could be combined to extend coverage, since variations in sequence of each epitope occur independently. For example, combining an Epitope I immunogen(s) (95%) with an Epitope II immunogen (96%) would result in antibodies in immunologically responsive subjects reactive with 99.8% of known HIV-1 Tat proteins. Thus, as one example, a composition of this invention contains one Epitope I (underlined)-Epitope II (double-underlined) fused peptide immunogen such as Cys-Glu-Pro-Val-Asp-Pro-Lys-Leu-Glu-Pro-Trp-Lys-Glu-Leu-Gly-Ile-Ser-Tyr-Gly-Arg-Lys-Lys-amide (SEQ ID NO: 67), coupled to carrier protein attached to Epitope I, or the same peptide (less the N-terminal Cys for coupling), synthesized as a multiple antigenic peptide, optionally coupled to a carrier protein. Alternatively, mixtures of two or more immunogens could be used as follows.

The Epitope I immunogens, with or without any Epitope II, III or IV or other optional immunogens, may be prepared and used in immunogenic compositions in a variety of forms, for example, chemically synthesized or as recombinant peptides, polypeptides, proteins, fusion proteins or fused peptides.

1. Synthetic Peptide/Protein Coupled to a Carrier

As one embodiment, a composition of the present invention may be a synthetic peptide, containing single or multiple copies of the same or different Epitope I immunogen amino acid sequences and/or Epitope II/III/IV immunogenic amino acid sequences, and optionally amino acid sequences of the optional immunogens, coupled to a selected carrier protein. In this embodiment of a composition of this invention, multiple above-described Epitope I amino acid sequences with or without flanking sequences, may be combined sequentially in a polypeptide and coupled to the same carrier. Alternatively, the Epitope I, II, III, or IV immunogens, may be coupled individually as peptides to the same or different carrier proteins, and the resulting immunogen-carrier constructs mixed together to form a single composition.

For this embodiment, the carrier protein is desirably a protein or other molecule which can enhance the immunogenicity of the selected immunogen. Such a carrier may be a larger molecule which has an adjuvanting effect. Exemplary conventional protein carriers include, without limitation, *E. coli* DnaK protein, galactokinase (galK, which catalyzes the first step of galactose metabolism in bacteria), ubiquitin, α-mating factor, β-galactosidase, and influenza NS-1 protein. Toxoids (i.e., the sequence which encodes the naturally occurring toxin, with sufficient modifications to eliminate its toxic activity) such as diphtheria toxoid and tetanus toxoid may also be employed as carriers. Similarly a variety of bacterial heat shock proteins, e.g., mycobacterial hsp-70 may be used. Glutathione reductase (GST) is another useful carrier. One of skill in the art can readily select an appropriate carrier.

In particularly desirable immunogen-carrier protein construct, one or more epitope immunogen and optional immunogen peptides/polypeptides may be covalently linked to a mycobacterial *E. coli* heat shock protein 70 (hsp70) (K. Suzue et al, J. Immunol., 156:873 (1996)). In another desirable embodiment, the composition is formed by covalently linking the immunogen-containing peptide or polypeptide sequences to diphtheria toxoid.

2. Multiple Antigenic Peptide

In yet another embodiment, the peptides or polypeptide epitope immunogens and any selected optional immunogens may be in the form of a multiple antigenic peptide ("MAP", also referred to as an octameric lysine core peptide) construct. Such a construct may be designed employing the MAP system described by Tam, Proc. Natl. Acad. Sci. USA, 85:5409–5413 (1988). This system makes use of a core matrix of lysine residues onto which multiple copies of the same Epitope I or optional immunogens of the invention are synthesized as described (D. Posnett et al., J. Biol. Chem., 263(4):1719–1725 (1988); J. Tam, "Chemically Defined Synthetic Immunogens and Vaccines by the Multiple Antigen Peptide Approach", Vaccine Research and Developments, Vol. 1, ed. W. Koff and H. Six, pp. 51–87 (Marcel Deblau, Inc., New York 1992)). Each MAP contains multiple copies of only one peptide. Therefore, e.g., an epitope composition of this invention can include a MAP in which the peptide or polypeptide epitope immunogen attached to the lysine core contains one or sequential repeats of the four amino acid sequences (SEQ ID NOS: 6–9) identified above. Multiple different MAPs may be employed to obtain any desired combination of Epitope I, II, III or IV sequences. Preferably these MAP constructs are associated with other T cell stimulatory sequences, or as pharmaceutical compositions, administered in conjunction with T cell stimulatory agents, such as known adjuvants.

3. Spacers

In either of the above compositions, e.g., as peptide/polypeptide-carrier constructs or MAPs, each peptide/polypeptide immunogen, or each amino acid sequence in the immunogen, may be optionally separated by optional amino acid sequences called "spacers". Spacers are sequences of between 1 to about 4 amino acids which are interposed between two sequences to permit linkage therebetween without adversely effecting the three dimensional structure of the immunogen. Spacers may also contain restriction endonuclease cleavage sites to enable separation of the sequences, where desired. Suitable spacers or linkers are known and may be readily designed and selected by one of skill in the art. Preferred spacers are sequences containing Gly and/or Ser amino acids.

F. Nucleic Acid Compositions of the Invention, Including a Synthetic Gene

Other embodiments of this invention include nucleic acid sequences, which encode the above-described peptide/polypeptide compositions, including the peptide and polypeptide immunogens of the compositions described above, including those peptides and polypeptides fused to carrier proteins. The nucleic acid sequences may also include sequences encoding the carrier proteins.

Thus, one preferred embodiment of the invention is a "synthetic gene" which encodes sequentially for one or more Epitope I immunogenic peptides/polypeptide. The synthetic gene preferably encodes two, three or all four Epitope I amino acid sequences (SEQ ID NOS: 6 through 9, respectively):

R1-Val-Asp-Pro-Arg-Leu-Glu-Pro-R2;
R1-Val-Asp-Pro-Lys-Leu-Glu-Pro-R2;

R1-Val-Asp-Pro-Ser-Leu-Glu-Pro-R2; and

R1-Val-Asp-Pro-Asn-Leu-Glu-Pro-R2.

The synthetic gene can also encode any selection of the optional immunogens identified above, and may include an Epitope II or III immunogen provided that the Epitope II or III peptide is fused to the C terminus of the Epitope I sequence and not further modified on its own C terminus. The synthetic gene may encode multiple copies of the same amino acid sequence, copies of multiple different immunogens or amino acid sequences, or multiple copies of multiple different immunogens or amino acid sequences. The synthetic gene may encode the selected amino acid sequences in an open reading frame with, or fused to, a nucleic acid sequence encoding a carrier protein. A further characteristic of the synthetic gene may be that it encodes a spacer between each sequence encoding an immunogen and/or between the sequence encoding an immunogen and the sequence encoding the carrier protein.

The synthetic gene of the present invention may also be part of a synthetic or recombinant molecule. The synthetic molecule may be a nucleic acid construct, such as a vector or plasmid which contains the synthetic gene encoding the protein, peptide, polypeptide, fusion protein or fusion peptide under the operative control of nucleic acid sequences encoding regulatory elements such as promoters, termination signals, and the like. Such synthetic molecules may be used to produce the polypeptidelpeptide immunogen compositions recombinantly.

The synthetic gene or synthetic molecules can be prepared by the use of chemical synthesis methods or preferably, by recombinant techniques. For example, the synthetic gene or molecules may contain certain preference codons for the species of the indicated host cell.

The synthetic gene or molecules, preferably in the form of DNA, may be used in a variety of ways. For example, these synthetic nucleic acid sequences may be employed to express the peptide/polypeptides of the invention in vitro in a host cell culture. The expressed immunogens, after suitable purification, may then be incorporated into a pharmaceutical reagent or vaccine.

Alternatively, the synthetic gene or synthetic molecule of this invention may be administered directly into a mammalian, preferably human subject, as so-called 'naked DNA' to express the protein/peptide immunogen in vivo in a patient. See, e.g., J. Cohen, Science, 259:1691–1692 (Mar. 19, 1993); E. Fynan et al., Proc. Natl. Acad. Sci., USA, 90:11478–11492 (Decemeber 1993);and J. A. Wolffet al., Biotechniques, 11:474–485 (1991), all incorporated by reference herein. The synthetic molecule, e.g., a vector or plasmid, may be used for direct injection into the mammalian host. This results in expression of the protein by host cells and subsequent presentation to the immune system to induce antibody formation in vivo.

G. Microorganisms that Express the Synthetic Gene

In still another aspect of the present invention, the synthetic genes or molecules of this invention may be incorporated into a non-pathogenic microorganism. The resulting microorganism, when administered to a mammalian host expresses and multiplies the expressed compositions of this invention in vivo to induce specific antibody formation. For example, non-pathogenic recombinant viruses or commensal bacterium which carry the compositions or synthetic genes of this invention and are useful for administration to a mammalian patient may be prepared by use of conventional methodology and selected from among known non-pathogenic microorganisms.

Among commensal bacterium which may be useful for exogenous delivery of the synthetic molecule to the patient, and/or for carrying the synthetic gene into the patient in vivo, include, for example, various strains of Streptococcus, e.g., *S. gordonii*, or *E. coli*, Bacillus, Streptomyces, and Saccharomyces.

Suitable non-pathogenic viruses which may be engineered to carry the synthetic gene into the cells of the host include poxviruses, such as vaccinia, adenovirus, canarypox, retroviruses and the like. A number of such non-pathogenic viruses are commonly used for human gene therapy, and as carrier for other vaccine agents, and are known and selectable by one of skill in the art.

H. Preparation or Manufacture of Compositions of the Invention

The compositions of the invention, and the individual polypeptides/peptides containing the Epitope I, II, III or Epitope IV or optional immunogens of this invention, the synthetic genes, and synthetic molecules of the invention, may be prepared conventionally by resort to known chemical synthesis techniques, such as described by Merrifield, J. Amer. Chem. Soc., 85:2149–2154 (1963). Alternatively, the compositions of this invention may be prepared by known recombinant DNA techniques by cloning and expressing within a host microorganism or cell a DNA fragment carrying a sequence encoding a peptide/polypeptide containing an Epitope I and/or optional immunogen and optional carrier protein. Coding sequences for the Epitope I and optional immunogens can be prepared synthetically (W. P. C. Stemmer et al, Gene, 164:49 (1995) or can be derived from viral RNA by known techniques, or from available cDNA-containing plasmids.

Combinations of these techniques may be used, such as for production of the synthetic gene, which may require assembly of sequential immunogens by conventional molecular biology techniques, and site-directed mutagenesis to provide desired sequences of immunogens. The product of the synthetic gene is then produced recombinantly. All of these manipulations may be performed by conventional methodology.

Systems for cloning and expressing the peptide/polypeptide compositions of this invention using the synthetic genes or molecules, include various microorganisms and cells which are well known in recombinant technology. These include, for example, various strains of *E. coli*, Bacillus, Streptomyces, and Saccharomyces, as well as mammalian, yeast and insect cells. Suitable vectors therefor are known and available from private and public laboratories and depositories and from commercial vendors. Currently, the most preferred host is a mammalian cell such as Chinese Hamster ovary cells (CHO) or COS-1 cells. These hosts may be used in connection with poxvirus vectors, such as vaccinia or swinepox. The selection of other suitable host cells and methods for transformation, culture, amplification, screening and product production and purification can be performed by one of skill in the art by reference to known techniques. See, e.g., Gething and Sambrook, Nature, 293:620–625 (1981).

Another preferred system includes the baculovirus expression system and vectors.

When produced by conventional recombinant means, the compositions of this invention, i.e., the polypeptide/peptides containing the indicated copies of the Epitope I immunogens and optional immunogens may be isolated either from the cellular contents by conventional lysis techniques or from cell medium by conventional methods, such as chromatography. See, e.g., Sambrook et al., Molecular Cloning. A Laboratory Manual., 2d Edit., Cold Spring Harbor Laboratory, New York (1989).

Suitable plasmid and viral vectors used either for production of the peptide/polypeptide components as DNA vaccines are well known to those of skill in the art and are not a limitation of the present invention. See, Sambrook et al., cited above and the references above to production of the protein. See, also International Patent Publication No. WO94/01139, published Jan. 20, 1994.

Briefly, the DNA encoding the selected peptide/polypeptide is inserted into a vector or plasmid which contains other optional flanking sequences, a promoter, an mRNA leader sequence, an initiation site and other regulatory sequences capable of directing the multiplication and expression of that sequence in vivo or in vitro. These vectors permit infection of patient's cells and expression of the synthetic gene sequence in vivo or expression of it as a protein/peptide or fusion protein/peptide in vitro.

The resulting composition may be formulated into a Epitope I composition with any number of optional immunogens and screened for efficacy by in vivo assays. Such assays employ immunization of an animal, e.g., a rabbit or a simian, with the composition, and evaluation of titers of antibody to the Tat proteins of HIV-1 or to synthetic detector peptides corresponding to variant Tat sequences (as shown in the examples below).

I. Antibody Compositions of the Invention

An isolated mammalian antibody composition which is directed against a peptide or polypeptide of the invention, as described above, is also an aspect of this invention. Such polyclonal antibody compositions are produced by immunizing a mammal with a peptide/polypeptide composition containing an assortment of Epitope I, II, III, and/or IV immunogens and optional immunogens, as described above. Suitable mammals include primates, such as monkeys; smaller laboratory animals, such as rabbits and mice, as well as larger animals, such as horse, sheep, and cows. Such antibodies may also be produced in transgenic animals. However, a desirable host for raising polyclonal antibodies to a composition of this invention includes humans.

The polyclonal antibodies raised in the mammal exposed to the composition are isolated and purified from the plasma or serum of the immunized mammal by conventional techniques. Conventional harvesting techniques can include plasmapheresis, among others.

Such polyclonal antibody compositions may themselves be employed as pharmaceutical compositions of this invention. Alternatively, other forms of antibodies may be developed using conventional techniques, including monoclonal antibodies, chimeric antibodies, humanized antibodies and fully human antibodies. See, e.g., Harlow et al., Antibodies A Laboratory Manual, Cold Spring Harbor Laboratory, (1988); Queen et al., Proc. Nat'l. Acad. Sci. USA, 86:10029–10032 (1989); Hodgson et al., Bio/Technology, 9:421 (1991); International PCT Application PCT/GB91/01554, Publication No. WO92/04381 and International PCT Application PCT/GB93/00725, Publication No. WO93/20210). Other anti-Tat antibodies may be developed by screening hybridomas or combinatorial libraries, or antibody phage displays (W. D. Huse et al., Science, 246:1275–1281 (1988)) using the polyclonal or monoclonal antibodies produced according to this invention and the amino acid sequences of the Epitope I, II, I, IV or optional immunogens.

These antibody compositions bind to greater than 95%, and preferably greater than 99% of known Tat protein variants of HIV-1, and prevent the Tat proteins from supporting further HIV-1 multiplication. Thus, these antibodies are useful in pharmaceutical methods and formulations described below.

J. Pharmaceutical Compositions of the Invention

As another aspect of this invention, a pharmaceutical composition useful for inducing antibodies that react with greater than 95%, preferably greater than 99%, of known HIV-1 Tat proteins and impair the multiplication of HIV-1 can comprise as its active agents, one or more of the peptides or polypeptides of Epitope I, II, III, or IV. Several desirable compositions include the following above-described components:

(a) a peptide/polypeptide immunogen which contains at least one, and preferably all four of the Epitope I amino acid sequences SEQ ID NOS: 6–9;

(b) a peptide/polypeptide immunogen which contains at least one of the Epitope II amino acid sequences;

(c) a peptide/polypeptide immunogen which contains at least one, and preferably three Epitope III amino acid sequences;

(d) a peptide/polypeptide immunogen which contains at least one Epitope IV amino acid sequence;

(e) a synthetic gene encoding one or more of Epitope I, Epitope II, Epitope III, or Epitope IV sequences as described above;

(f) a synthetic molecule described above;

(g) a recombinant virus carrying the synthetic gene or molecule; and (h) a commensal bacterial carrying the synthetic gene or molecule.

The selected active component(s) is present in a pharmaceutically acceptable carrier, and the composition may contain additional ingredients. Pharmaceutical formulations containing the compositions of this invention may contain other active agents, such as T cell stimulatory agents for the MAPs, adjuvants and immunostimulatory cytokines, such as IL-12 and other well-known cytokines, for the protein/peptide compositions. All of these pharmaceutical compositions can operate to lower the viral levels of a mammal.

As pharmaceutical compositions, these compositions comprising Epitope I and/or II, and/or III, and/or IV amino acid sequences with optional immunogenic amino acid sequences are admixed with a pharmaceutically acceptable vehicle suitable for administration as a protein composition for prophylaxis or treatment of virus infections. These proteins may be combined in a single pharmaceutical preparation for administration. Suitable pharmaceutically acceptable carriers for use in an immunogenic proteinaceous composition of the invention are well known to those of skill in the art. Such carriers include, for example, saline, buffered saline, a selected adjuvant, such as aqueous suspensions of aluminum and magnesium hydroxides, liposomes, oil in water emulsions and others. Suitable adjuvants may also be employed in the protein-containing compositions of this invention. The present invention is not limited by the selection of the carrier or adjuvant.

Suitable vehicles for direct DNA, plasmid nucleic acid, or recombinant vector administration include, without limitation, saline, or sucrose, protamine, polybrene, polylysine, polyrations, proteins, $CaPO_4$ or spermidine. See e.g, International Patent Publication No. WO94/01139 and the references cited above.

The peptide/polypeptide compositions and synthetic genes or molecules in vivo are capable of eliciting in an immunized host mammal, e.g., a human, an immune response capable of interdicting greater than about 95 to about 99% of known extracellular Tat protein variants from HIV-1 and thereby lowering the viral levels.

Yet another pharmaceutical composition useful for impairing the multiplication of HIV-1 comprises an antibody composition as described in detail above. In a pharmaceutical composition, the antibodies may be carried in a saline solution or other suitable carrier. The antibody compositions are capable of providing an immediate, exogenously provided interdiction of Tat.

The preparation of these pharmaceutically acceptable compositions, from the above-described components, having appropriate pH isotonicity, stability and other conventional characteristics is within the skill of the art.

K. Method of the Invention-Impairing Multiplication of HIV-1

According to the present invention, a method for reducing the viral levels of HIV-1 involves exposing a human to the Tat antibody-inducing pharmaceutical compositions described above, actively inducing antibodies that react with greater than 95%, preferably greater than 990%, of known HIV-1 Tat proteins, and impairing the multiplication of the virus in vivo. This method is appropriate for an HIV-1 infected subject with a competent immune system, or an uninfected or recently infected subject. The method induces antibodies which react with HIV-1 Tat proteins, which antibodies reduce viral multiplication during any initial acute infection with HIV-1 and minimize chronic viremia leading to AIDS. This method also lowers chronic viral multiplication in infected subjects, again minimizing progression to AIDS.

In one embodiment, the pharmaceutical compositions may be therapeutically administered to an HIV-1 infected human with a competent immune system for treatment or control of viral infection. Such an infected human may be asymptomatic. In a similar embodiment, the pharmaceutical compositions may be administered to an uninfected human for prophylaxis.

In these two instances, the pharmaceutical compositions preferably contain the peptide/polypeptide compositions, the synthetic genes or molecules, the recombinant virus or the commensal recombinant bacterium. Each of these active components of the pharmaceutical composition actively induces in the exposed human the formation of anti-Tat antibodies which block the transfer of Tat from infected cells to other infected or uninfected cells. This action reduces the multiplicity of infection and blocks the burst of HIV-1 viral expansion, and thus lowers viral levels. In already infected patients, this method of reduction of viral levels can reduce chronic viremia and progression to AIDS. In uninfected humans, this administration of the compositions of the invention can reduce acute infection and thus minimize chronic viremia leading to progression to AIDS.

Yet another aspect of the invention is a method for reducing the viral levels of HIV-1 by administering to a human, who is incapable of mounting an effective or rapid immune response to infection with HIV-1, a pharmaceutical composition containing the antibody compositions described above. The method can involve chronically administering the composition. Among such patients suitable for treatment with this method are HIV-1 infected patients who are immunocompromised by disease and unable to mount a strong immune response. In later stages of HIV infection, the likelihood of generating effective titers of antibodies is less, due to the immune impairment associated with the disease. Also among such patients are HIV-1 infected pregnant women, neonates of infected mothers, and unimmunized patients with putative exposure (e.g., a human who has been inadvertently "stuck" with a needle used by an HIV-1 infected human).

For such patients, the method of the invention preferably employs as the pharmaceutical composition the antibody composition of the invention, which is a polyclonal antibody composition prepared in other mammals, preferably normal humans. Alternatively, the other forms of antibody described above may be employed. These antibody compositions are administered as passive immunotherapy to inhibit viral multiplication and lower the viral load. The exogenous antibodies which react with greater than 95%, preferably greater than 99%, of known Tat proteins from HIV-1 provide in the patient an immediate interdiction of the transfer of Tat from virally infected cells to other infected or uninfected cells. According to this method, the patient may be chronically treated with the antibody composition for a long treatment regimen.

In each of the above-described methods, these compositions of the present invention are administered by an appropriate route, e.g., by the subcutaneous, oral, intravenous, intraperitoneal, intramuscular, nasal, or inhalation routes. The presently preferred route of administration is intramuscular for the immunizing (active induction) compositions and intravenous or intramuscular for the antibody (passive therapy) compositions. The recombinant viral vectors or naked DNA is preferably administered i.m.; however, other certain recombinant viral vectors and/or live commensal bacteria may be delivered orally.

The amount of the protein, peptide or nucleic acid sequences of the invention present in each vaccine dose is selected with regard to consideration of the patient's age, weight, sex, general physical condition and the like. The amount of active component required to induce an immune response, preferably a protective response, or produce an exogenous effect in the patient without significant adverse side effects varies depending upon the pharmaceutical composition employed and the optional presence of an adjuvant (for the protein-containing compositions).

Generally, for the compositions containing protein/peptide, fusion protein, MAP or coupled protein, or antibody composition, each dose will comprise between about 50 $\mu$g to about 2 mg of the peptide/polypeptide immunogens per mL of a sterile solution. A more preferred dosage may be about 500 $\mu$g of immunogen. Other dosage ranges may also be contemplated by one of skill in the art. Initial doses may be optionally followed by repeated boosts, where desirable The antibody compositions of the present invention can be employed in chronic treatments for subjects at risk of acute infection due to needle sticks or maternal infection. A dosage frequency for such "acute" infections may range from daily dosages to once or twice a week i.v. or i.m., for a duration of about 6 weeks. The antibody compositions of the present invention can also be employed in chronic treatments for infected patients, or patients with advanced HIV. In infected patients, the frequency of chronic administration may range from daily dosages to once or twice a week i.v. or i.m., and may depend upon the half-life of the immunogen (e.g., about 7–21 days). However, the duration of chronic treatment for such infected patients is anticipated to be an indefinite, but prolonged period.

Alternatively, compositions of this invention may be designed for direct administration of synthetic genes or molecules of this invention as "naked DNA". As with the protein immunogenic compositions, the amounts of components in the DNA and vector compositions and the mode of administration, e.g., injection or intranasal, may be selected and adjusted by one of skill in the art. Generally, each dose will comprise between about 50 $\mu$g to about 1 mg of immunogen-encoding DNA per mL of a sterile solution.

For recombinant viruses containing the synthetic genes or molecules, the doses may range from about 20 to about 50 ml of saline solution containing concentrations of from about $1\times10^7$ to $1\times10^{10}$ pfu/ml recombinant virus of the present invention. A preferred human dosage is about 20 ml saline solution at the above concentrations. However, it is understood that one of skill in the art may alter such dosages depending upon the identity of the recombinant virus and the make-up of the immunogen that it is delivering to the host.

The amounts of the commensal bacteria carrying the synthetic gene or molecules to be delivered to the patient will generally range between about $1\times10^3$ to about $1\times10^{12}$ cells/kg. These dosages, will of course, be altered by one of skill in the art depending upon the bacterium being used and the particular composition containing Epitope I, or Epitope II or Epitope III or Epitope IV and optional immunogens being delivered by the live bacterium.

Thus, the compositions of this invention are designed to retard or minimize infection by the selected virus of an uninfected mammal, e.g., human. Such compositions thus have utility as vaccines. Anti-Tat protein antibodies are not reactive with the HIV-1 proteins used in diagnostic assays to detect seroconversion after infection. Thus, subjects treated with the compositions of this invention would not be stigmatized with false-positive tests for HIV-1 infection, and it would remain possible to detect seroconversion if treated subjects did become infected with HIV-1.

Providing a mammal with the compositions of this invention, whether as a protein/peptide-containing composition or by administration of a novel nucleic acid sequence encoding the immunogen, affords a radically different strategy for AIDS vaccination because it permits the lowering of viral levels by biological interdiction of greater than about 95%, and preferably greater than about 99%, of known Tat protein variants of HIV-1, lowering multiplication of HIV-1.

The use of the Tat immunogen-containing compositions has a particularly desirable advantage in contrast to other treatments and prophylactic methods employed against such viruses. Because interdiction of the Tat protein extracellularly inhibits the multiplication of all HIV quasi-species or strains indiscriminately, it does not create a selective pressure on the parent virus itself for selection of mutant virus variants. Thus, blocking the uptake of Tat protein by the patient's cells not only reduces the level of viremia, but does so in a manner that precludes the selection of "escape variants".

Additionally, the invention comprises a method of actively treating asymptomatic HIV-1 infected subjects with viremia, since during the course of the disease, extracellular Tat protein likely contributes to the persistent infection and immune abnormalities that are present at this stage of HIV-1 infection. Interdiction of extracellular Tat protein by antibodies induced by immunization according to this invention can reduce viremia with more effective immune control, and result in delay or prevention of progression to AIDS.

The mechanism of the present invention as described above is useful in impeding the course of viral infection and producing desirable clinical results. More specifically, the compositions of this invention are capable of reducing viremia in patients already infected with the virus by blocking further uptake of the Tat protein by uninfected cells. The compositions of the present invention, used either alone or in conjunction with other therapeutic regimens for HIV infected patients, are anticipated to assist in the reduction of viremia and prevention of clinical deterioration.

For such therapeutic uses, the formulations and modes of administration are substantially identical to those described specifically above and may be administered concurrently or simultaneously with other conventional therapeutics for the specific viral infection. For therapeutic use or prophylactic use, repeated dosages of the immunizing compositions may be desirable, such as a yearly booster or a booster at other intervals.

L. Diagnostic Kits of this Invention

The peptides and polypeptides described above can also be employed as reagents of a kit useful for the measurement and detection of titers and specificities of antibodies induced by vaccination with the compositions described above. The kit of the invention can include one or more peptides of Epitopes I through IV. In one embodiment, each peptide has on its N terminus the protein biotin and a spacer, e.g.,-Ser-Gly-Ser-Gly- (SEQ ID NO: 30). Alternatively, the peptide may have on its C terminus a spacer, e.g., -Gly-Ser-Gly-Ser- (SEQ ID NO: 90), and the protein biocytin. These embodiments enable the peptides to be bound to an avidincoated solid support, e.g., a plate or beads. Of course, other binding agents known to those of skill in the diagnostic assay art may also be employed for the same purposes. Also provided in the kit are, labeled reagents which detect the binding of antibody to the immobilized Epitope peptides, such as a goat anti-human immunoglobulin or the like. The label on the reagent may be selected from the many known diagnostic labels, such as radioactive compounds, fluorescent compounds and proteins, colorimetric enzymes, etc. The kit thus also contains miscellaneous reagents and apparatus for reading labels, e.g., certain substrates that interact with an enzymatic label to produce a color signal, etc., apparatus for taking blood samples, as well as appropriate vials and other diagnostic assay components. One of skill in the art may also readily select other conventional diagnostic components for this kit.

Such kits and reagents may be employed in a method for detecting the titers and reactivity patterns of antibodies in subjects vaccinated with the compositions of this invention. A method for determining the presence and or titer of antibodies induced by immunization to a Tat immunogen includes the steps of contacting a biological sample from an immunized subject, e.g., a body fluid, preferably blood, serum or plasma, but also possibly urine, saliva and other fluids or tissue, with one or more of the binding sequences of Epitope I, II, III or IV, preferably immobilized on a solid support, such as a plate or beads. The Epitope I, II, III or IV binding sequences employed in this method may be the minimal binding regions, unmodified. Therefore, such sequences include -Val-Asp-Pro-Y-Leu-Glu-Pro- (SEQ ID NO: 86) or -Glu-Pro-Val-Asp-Pro-Y-Leu-Glu-Pro- (SEQ ID NO: 124), wherein Y is selected from the group consisting of Arg, Lys, Ser and Asn; and/or -Lys-X-Leu-Gly-Ile-Ser-Tyr-Gly-Arg-Lys-Lys- (SEQ ID NO: 87), wherein X is selected from the group consisting of Gly or Ala; and/or -Arg-Arg-X-Z-A-Y-Ser- (SEQ ID NO: 88), wherein X is selected from the group consisting of Ala, Pro, Ser and Gln; wherein Y is selected from the group consisting of Asp, Asn, Gly and Ser; wherein Z is selected from the group consisting of Pro and His; wherein A is selected from the group consisting of Gln and Pro; and/or -Ser-Gln-X-His-Gln-Y-Ser-Leu-Ser-Lys-Gln-Pro- (SEQ ID NO: 89), wherein X is selected from the group consisting of Asn and Thr; wherein Y is selected from the group consisting of Ala and Val.

Once the biological sample is exposed to the immobilized peptides for a sufficient time, the support is washed to eliminate any material from the biological sample which is not bound to the peptides. Such washing steps are conventional in diagnostic assays, and performed with saline. If antibodies to Epitopes I, or II, or III, or IV, or a combination thereof, were induced in the subject by the above-described treatment, the immobilized peptides have been bound with an antibody from the biological sample. Thereafter, a labeled reagent is added to the material on the support to detect the binding between the peptides on the solid support and antibody in said biological sample. Preferably, such a reagent is an anti-human immunoglobulin, such as goat anti-human immunoglobulin. The label is selected from among a wide array of conventionally employed diagnostic labels, as discussed above. In one embodiment, the label can be a colorimetric enzyme, which upon contact with a substrate produces a detectable color signal. The presence and/or intensity of the color provides evidence of the induction of antibody in the treated subject. This assay may be employed to determine the efficacy of the immunization, as well as to monitor immune status of a patient.

Again, the selection of particular assay steps, as well as a variety of detectable label systems, is well within the skill of the art. Such selection is routine and does not limit the present invention.

M. Advantages of the Invention

One of the advantages of the compositions of this invention is the small number of immunogens required for inclusion into a composition of this invention to cross-react with greater than 95 to greater than 99% of known Tat protein variants of HIV-1 of the common B subtype. As mentioned above, an immunogen of Epitope I in which Y was Lys (SEQ ID NO: 7) could suffice for full cross-reactivity to all four position Y variants, and could be used alone in an immunogenic composition. Alternatively, as illustrated in the examples below, the Epitope I immunogenic composition containing all four Epitope I amino acid sequences cross-reacts with 387 of 399 Tat proteins of HIV-1 of the common B subtype, as well as with all 18 Tat protein sequences from less frequent non-B subtypes of HIV-1. Thus, a single composition may be usefully employed in protecting against or treating infection, caused by the vast majority of HIV-1 strains that can be encountered.

Further, having identified the precise epitopes on Tat against which binding is desired (i.e., AA2-10, AA41-51, or AA56-62 of SEQ ID NO: 1) new desirable Tat peptide immunogens from newly occurring HIV-1 strains or newly discovered strains may be easily identified using the methods described herein, and included in the compositions. This flexibility enables the compositions of this invention to be useful prophylactically against any new strain or strains of HIV-1 identified in the future. In view of the teachings herein, one of skill in the art is expected to be readily able to incorporate new combinations of Tat immunogens (and the nucleic acid constructs encoding them) into the compositions.

For example, the use of conventional techniques such as PCR and high density oligonucleotide arrays (M. J. Kozal et al, Nature Med., 2:753 (1996)) enables one of skill in the art to obtain the amino acid sequences of a large array of HIV-1 Tat proteins representing variants of clinical isolates of HIV-1 strains and subtypes. Using such techniques permits determination of other variants of the HIV-1 B subtype as well as other subtypes in undeveloped countries, which have not been so intensively studied to date. The determination of new Tat sequences will enable ready inclusion of the corresponding peptides as immunogens into compositions of this invention, allowing the induction of an antibody response against other rare Tat proteins of HIV-1.

Cross-reactivity studies with antibodies raised to synthetic peptides corresponding to each Tat variant can be utilized to eliminate the need for immunizing with Tat variants in which the sequence changes are immunologically silent, in that these peptides are strongly bound by antibodies to the consensus sequence or other variants.

The following examples illustrate preferred methods for preparing the compositions of the invention and utilizing these compositions to induce antibodies to Tat proteins of the virus in an immunized host. These examples are illustrative only and do not limit the scope of the invention.

EXAMPLE 1

Immunological Studies on Minimal Tat Protein Amino Acid Sequences Necessary for Binding to Antibody for Epitope I in HIV-1 Tat Protein A peptide corresponding to amino acids 4–16 of SEQ ID NO: 1 illustrated in FIG. 1 was synthesized as described below. This sequence is among the most frequent sequence representation at these positions in 31 Tat protein sequences of the common B subtype reported in the NIAID HIV database. This sequence was chosen as a putative immunogen, named Epitope I.

A. Peptide Synthesis-Immunizing Peptides

The amino acid sequence of this immunogen -Val-Asp-Pro-Arg-Leu-Glu-Pro-Trp-Lys-His-Pro-Gly-Ser- (SEQ ID NO: 28) was synthesized by solid phase methodology on polypropylene pegs according to the methods of H. M.

Geysen et al, J. Immunol. Meth., 102:259 (1987), with an N-terminal cysteinyl being incorporated to facilitate coupling to a carrier protein. The N-terminus was left as a free amine and the C-terminus was amidated in the immunizing peptides for most of the experiments for which data is reported in Table 2 below. Immunizing peptides were generally purified to greater than 95% purity by reverse phase HPLC, and purity was further confirmed by mass spectometry (MS).

Immunizing peptides were covalently coupled to diphtheria toxoid (DT) carrier protein via the cysteinyl side chain by the method of A. C. J. Lee et al., Molec. Immunol., 17:749 (1980), using a ratio of 6–8 moles peptide per mole of diphtheria toxoid.

B. Peptide Synthesis-Detector Peptides

A peptide corresponding to the amino acid sequence of the immunogen peptide was synthesized by the method of Geysen, cited above, for use in ELISA assays for detection of reactivity and cross-reactivity. Additional peptides with N- and C-terminal truncations were also synthesized.

For most of the experiments reported below in Tables 2 and 3, detector peptides had an N-terminal -Ser-Gly-Ser-Gly- (SEQ ID NO: 30) added, with biotinylation of the new N-terminus, and the C-terminal remained a free acid. The C-terminal detecting peptides for some of these experiments had been inadvertently synthesized with an amidated C-terminus, which may have led to a spuriously high binding for (SEQ AD NO: 32) -Asp-Pro-Arg-Leu-Glu-Pro-Trp-Lys-His-Pro-Gly-Ser- reported in Tables 2 and 3 below. Therefore, several peptides were resynthesized with appropriate C-terminal groups and the pertinent parts of the experiment were repeated with antibody to -Val-Asp-Pro-Arg-Leu-Glu-Pro-Trp-Lys-His-Pro-Gly-Ser- (SEQ ID NO:28), and the results reported in Table 3 below. These detector peptides had a purity exceeding 70% by mass spectometry and were not purified further.

C. Immunization of Rabbits

The peptide conjugates were taken up in purified water and emulsified 1:1 with complete Freund's adjuvant (CFA) or incomplete Freund's adjuvant (IFA) (ANTIBODIES-A LABORATORY MANUAL, Eds. E. Harlow and P. Lane, Cold Spring Harbor Laboratory (1998)). Total volume per rabbit was 1 ml, and this contained 100 µg of peptide coupled to DT.

Two rabbits were used for the immunizing peptide, with the initial intramuscular (IM) injection with conjugate in CFA and a subsequent IM boost at 2 weeks with conjugate in IFA. A pre-bleed was drawn before the first injection and larger bleeds were taken 3 and 5 weeks after the booster injection.

D. ELISA Determination of Binding of Antiserums to Biotinylated Peptides

These assays were performed as described by H. M. Geysen et al., Proc. Natl. Acad. Sci. USA, 81:3998 (1983). Briefly, using Nunc Immuno Maxisorb™ 96 well plates, biotinylated peptides were bound to streptavidin coated plates and, with washing with phosphate buffered saline (PBS) between steps, successive incubations were performed with antiserum dilutions and horseradish peroxidase conjugated anti-rabbit immunoglobulin to detect bound antibody. Plates were developed with ABTS, with an O.D. reading at 405 nm. Absorbance greater than O.D. 1.0 was taken as positive and titers were determined from doubling dilutions of each antiserum. The geometric mean titer (GMT) was calculated for each antiserum pair for a given immunogen.

TABLE 2

| Detector Sequence* | Antiserum to Epitope I: -Val-Asp-Pro-Arg-Leu-Glu-Pro-Trp-Lys-His-Pro-Gly-Ser-; GMT (% binding versus immunogen) | SEQ ID NO. |
|---|---|---|
| -Val-Asp-Pro-Arg-Leu-Glu-Pro-Trp-Lys-His-Pro-Gly-Ser- | 65,885 (100) | 31 |
| -Asp-Pro-Arg-Leu-Glu-Pro-Trp-Lys-His-Pro-Gly-Ser- | 83,753 (127) | 32 |
| -Val-Asp-Pro-Arg-Leu-Glu-Pro-Trp- | 96,627 (147) | 33 |
| -Val-Asp-Pro-Arg-Leu-Glu-Pro- | 80,960 (123) | 34 |
| -Val-Asp-Pro-Arg-Leu-Glu- | 32,016 (49) | 35 |

*Substitution of Asp to Gly, Ala or His reduced titer to <1% (See Example 2)

TABLE 3

| N Terminus | Detector Sequences | C Terminus | % binding | SEQ ID No |
|---|---|---|---|---|
| N0 | Val-Asp-Pro-Arg-Leu-Glu-Pro-Trp-Lys-His-Pro-Gly-Ser-Gln-Pro-Lys-Thr-Ala-OH | C + 11 | 124 | 71 |
| N0 | Val-Asp-Pro-Arg-Leu-Glu-Pro-Trp-Lys-His-Pro-Gly-Ser-OH | C + 6 | 100 | 28 |
| N0 | Val-Asp-Pro-Arg-Leu-Glu-Pro-Trp-OH | C + 1 | 120 | 33 |
| N0 | Val-Asp-Pro-Arg-Leu-Glu-Pro-Trp-NH$_2$ | C + 1 | 134 | 92 |
| N0 | Val-Asp-Pro-Arg-Leu-Glu-Pro-NH$_2$ | C0 | 116 | 93 |
| N0 | Val-Asp-Pro-Arg-Leu-Glu-NH$_2$ | C − 1 | 47 | 94 |
| N0 | Val-Asp-Pro-Arg-Leu-OH | C − 2 | 5 | 95 |
| N − 1 | Asp-Pro-Arg-Leu-Glu-Pro-Trp-OH | C + 1 | 65 | 96 |
| N − 2 | Gly-Pro-Arg-Leu-Glu-Pro-Trp-OH | C + 1 | 1 | 97 |
| N − 2 | Ala-Pro-Arg-Leu-Glu-Pro-Trp-OH | C + 1 | 1 | 98 |

ELISA results reported in Tables 2 and 3 demonstrated that the antibodies to the first immunogen were reacting with the sequence-Asp-Pro-Arg-Leu-Glu-Pro (AA 5–10 of SEQ ID NO: 1). N- or C-terminal truncation of these sequences reduced the ELISA titer. From the results of Tables 2 and 3 taken together, the N-terminal Val of the Epitope I peptide makes a small contribution to antibody binding (deletion gives 65% of binding). Thus the definition of the primary antibody binding region of HIV-1 Tat, referred to herein as Epitope I, is: -Val-Asp-Pro-Arg-Leu-Glu-Pro- (SEQ ID NO:34).

E. HIV-1 Tat Epitope I Minimal Sequence Analysis

The following experiment was performed using as the immunizing peptide sequence: Val-Asp-Pro-Arg-Leu-Glu-Pro-Trp-Lys-His-Pro-Gly-Ser-NH$_2$ (SEQ ID NO: 28). As demonstrated by the results in Table 3, the minimal sequence of Epitope I with maximal binding of antibody is confirmed as Val-Asp-Pro-Arg-Leu-Glu-Pro (SEQ ID NO:34). The variations in binding with C-terminal extensions are not significant. The truncation of N-terminal Val or C-terminal Pro lead to modest reduction of binding titers, but truncating beyond this leads to almost complete loss of specific binding, indicating that Asp-Pro-Arg-Leu-Glu (amino acids 5–9 of SEQ ID NO: 1) are the most important amino acids to create interactions with specific antibody (See, e.g., FIG. 3). GMT is reported as % of GMT on detector peptide containing the immunogen sequence.

F. Effects of Epitope I Immunogen Extension on Antibody Titers

N terminal extension of the epitope sequence in the immunogen does not affect immunogenicity. In contrast, C terminal extension up to Val-Asp-Pro-Arg-Leu-Glu-Pro-Trp-Lys-His-Pro-Gly-Ser-NH$_2$ (SEQ ID NO: 28) results in a 10-fold enhancement on titer. The present optimal immunizing sequence appears to be SEQ ID NO: 28. GMT on SEQ ID NO: 28 is reported as % of GMT of antiserums to SEQ ID NO: 28 on this peptide, as shown in Table 4.

TABLE 4

| N Terminus | Immunogen Sequences | C Terminus | % binding | SEQ ID # |
|---|---|---|---|---|
| N0 | Val-Asp-Pro-Arg-Leu-Glu-Pro-Trp-Lys-His-Pro-Gly-Ser-NH$_2$ | C + 6 | 100 | 28 |
| N + 2 | Glu-Pro-Val-Asp-Pro-Arg-Leu-Glu-Pro-Trp-Lys-His-Pro-Gly-Ser-OH | C + 6 | 105 | 99 |
| N0 | Val-Asp-Pro-Arg-Leu-Glu-Pro-Trp-Lys-His-Pro-OH | C + 4 | 10 | 100 |
| N0 | Val-Asp-Pro-Arg-Leu-Glu-Pro-Trp-Lys-OH | C + 2 | 67 | 101 |
| N0 | Val-Asp-Pro-Arg-Leu-Glu-Pro-NH$_2$ | C0 | 9 | 102 |

G. Binding Pattern of Antibodies Induced by N-terminally Extended Immunogens

The binding of antiserums to Epitope I immunogens with N-terminal sequence extensions through the N-terminal Met were examined on detector peptides with full length and N- or C-terminal truncation. In these instances some of the immunizing peptides were synthesized with C-terminal Cys-amide for coupling to the carrier protein and corresponding detector peptides were synthesized with a C-terminal-Gly-Ser-Gly-Ser-biocytin-amide (SEQ ID NO: 91) for binding to avidin coated plates.

TABLE 5

Antiserum to Met-Glu-Pro-Val-Asp-Pro-Arg-Leu-Glu-Pro-Trp-Lys-His-Pro-Gly-Ser-Gln-Pro-Lys-Thr-Ala- (amino acids 1–21 of SEQ ID NO: 1).
Titers on N-terminal truncation peptides

| Detector Peptide | Titer | % titer on longest peptide |
|---|---|---|
| Met-Glu-Pro-Val-Asp-Pro-Arg-Leu-Glu-Pro (amino acids 1–10 of SEQ ID NO: 1) | 61,000 | 100 |
| -Glu-Pro-Val-Asp-Pro-Arg-Leu-Glu-Pro (amino acids 2–10 of SEQ ID NO: 1) | 54,000 | 89 |
| -Pro-Val-Asp-Pro-Arg-Leu-Glu-Pro (amino acids 3–10 of SEQ ID NO: 1) | 37,000 | 61 |
| -Val-Asp-Pro-Arg-Leu-Glu-Pro (amino acids 4–10 of SEQ ID NO: 1) | 19,000 | 22 |
| -Pro-Arg-Leu-Glu-Pro (amino acids 6–10 of SEQ ID NO: 1) | 9,000 | 11 |
| -Arg-Leu-Glu-Pro (amino acids 7–10 of SEQ ID NO: 1) | 581 | <1 |

TABLE 6

Antiserum to Glu-Pro-Val-Asp-Pro-Arg-Leu-Glu-Pro-Trp-Lys-His-Pro-Gly-Ser (amino acids 2–16 of SEQ ID NO: 1).
Titers on C-terminal truncation peptides

| Detector Peptide | Titer peptide | % titer on longest peptide |
|---|---|---|
| Met-Glu-Pro-Val-Asp-Pro-Arg-Leu-Glu-Pro (amino acids 1–10 of SEQ ID NO: 1) | 112,000 | 100 |
| Met-Glu-Pro-Val-Asp-Pro-Arg-Leu-Glu (amino acids 1–9 of SEQ ID NO: 1) | 27,000 | 24 |
| Met-Glu-Pro-Arg-Leu (amino acids 1–5 of SEQ ID NO: 1) | 6,000 | 5 |

From the above data it is evident that N-terminal extension of the immunizing Epitope I peptide extends the antibody binding region through Glu$_2$ of the HIV-1 Tat protein sequence.

TABLE 7

| Immunizing Peptide | Titer on: Met-Glu-Pro-Val-Asp-Pro-Arg-Leu-Glu-Pro (amino acids 1–10 of SEQ ID NO: 1) | Titer on: Val-Asp-Pro-Arg-Leu-Glu-Pro (amino acids 4–10 of SEQ ID NO: 1) |
|---|---|---|
| Val-Asp-Pro-Arg-Leu-Glu-Pro-Trp-Lys-His-Pro-Gly-Ser (amino acids 4–16 of SEQ ID NO: 1) | 79,000 | 79,000 |
| Glu-Pro-Val-Asp-Pro-Arg-Leu-Glu-Pro-Trp-Lys-His-Pro-Gly-Ser (amino acids 2–16 of SEQ ID NO: 1) | 70,000 | 42,000 |
| Met-Glu-Pro-Val-Asp-Pro-Arg-Leu-Glu-Pro-Trp-Lys-His-Pro-Gly-Ser-Gln-Pro-Lys-Thr-Ala- (amino acids 1–21 of SEQ ID NO: 1) | 61,000 | 19,000 |

These data show that very similar total anti-Tat antibody titers are obtained with the various N-terminal immunogens but with a slightly different distribution of the binding regions.

EXAMPLE 2

Sequence Variations in Epitope I of HIV-1 Tat Protein and Immunological Cross-reactivities of Antiserums to these Sequences Variations in the sequence of Tat protein AA 5–10 of SEQ ID NO: 1 were analyzed in sequences available in HUMAN RETROVIRUSES and AIDS 1996, published by the Theoretical Biology and Biophysics Group of the Los Alamos National Laboratory, Los Alamos, N.Mex., and additional sequences kindly obtained from GenBank by Esther Guzman of the Los Alamos Laboratory.

A. Variations in Sequences 399 aa 5–10 Tat hexapeptide sequences of the common B subtype of HIV-1 were obtained, as were 18 from the non-B subtypes (6 from subtype A, 2 from subtype C, 7 from subtype D, 2 from subtype F and 1 from subtype U).

For the B subtype, 386 of the total 399 (97%) hexapeptides had either Arg (289, 74%), or Lys (45, 11%), or Ser (36, 9%) or Asn (16, 4%) in position 3 as the only variation in the hexapeptides. The remaining variations (3%) comprised:

-<u>Gly</u>-Pro-Arg-Leu-Glu-Pro- (4) (SEQ ID NO: 11),

-Asp-Pro-<u>Gly</u>-Leu-Glu-Pro- (2) (SEQ ID NO: 14), and single examples of:

-Asp-<u>His</u>-Arg-Leu-Glu-Pro- (SEQ ID NO: 41),
-<u>Ala</u>-Pro-Arg-Leu-Glu-Pro- (SEQ ID NO: 12),
-<u>His</u>-Pro-Arg-Leu-Glu-Pro- (SEQ ID NO: 13),
-Asp-Pro-Arg-<u>Ile</u>-Glu-Pro- (SEQ ID NO: 15),
-Asp-Pro-Arg-Leu-<u>Gly</u>-Pro- (SEQ ID NO: 16),
-Asp-Pro-Arg-Leu-Glu-<u>Ala</u>- (SEQ ID NO: 17) and
-<u>Asn</u>-Pro-Ser-Leu-Glu-Pro- (SEQ ID NO: 18).

For the 18 non-B subtype sequences, 2 had Arg, 1 had Lys, 2 had Ser and 9 had Asn at position 3 of the hexapeptides aa5–10, and other variants were -Asp-Pro-Asn-Leu-<u>Asp</u>-Pro- (2) (SEQ ID NO: 42) and single examples of -Asp-Pro-Asn-<u>Ile</u>-Glu-Pro- (SEQ ID NO: 43) and
-Asp-Pro-Asn-Leu-Glu-<u>Ser</u>- (SEQ ID NO: 44).

B. Assessment of Immunological Reactivity and Cross-reactivity of the Four Primary Immunogens Immunizing and detector sequences were synthesized, as described in Example 1, for the following sequences (SEQ ID NOS: 28 and 45 through 47, respectively):

-Val-<u>Asp-Pro-Arg-Leu-Glu-Pro</u>-Trp-Lys-His-Pro-Gly-Ser-,
-Val-<u>Asp-Pro-Lys-Leu-Glu-Pro</u>-Trp-Lys-His-Pro-Gly-Ser-,
-Val-<u>Asp-Pro-Ser-Leu-Glu-Pro</u>-Trp-Lys-His-Pro-Gly-Ser-,
-Val-<u>Asp-Pro-Asn-Leu-Glu-Pro</u>-Trp-Lys-His-Pro-Gly-Ser-.

Rabbits were immunized and the antiserums were tested by ELISA, as described in Example 1, for reactivity and cross-reactivity. Self-reactivities are summarized in Table 8.

TABLE 8

| Immunogen and detector sequence | GMT | SEQ ID NO |
|---|---|---|
| -Val-<u>Asp-Pro-Arg-Leu-Glu-Pro</u>-Trp-Lys-His-Pro-Gly-Ser- | 88,000 | 28 |
| -Val-<u>Asp-Pro-Lys-Leu-Glu-Pro</u>-Trp-Lys-His-Pro-Gly-Ser- | 132,000 | 45 |
| -Val-<u>Asp-Pro-Ser-Leu-Glu-Pro</u>-Trp-Lys-His-Pro-Gly-Ser- | 166,355 | 46 |
| -Val-<u>Asp-Pro-Asn-Leu-Glu-Pro</u>-Trp-Lys-His-Pro-Gly-Ser- | 173,097 | 47 |

Cross-reactivities between these primary immunogens with varying amino acid residues at position 3 of Epitope I are displayed in Table 9. Note that the results reported below are averages with one poorly reactive antiserum.

TABLE 9

Antiserums to primary immunogens
(figures denote % reactivity v. self-reactivity)

| Detectors | Arg3 | Lys3 | Ser3 | Asn3 |
|---|---|---|---|---|
| Arg3 | 100 | 49 | 3 | 4 |
| Lys3 | 24 | 100 | 6 | 5 |
| Ser3 | 11 | 16 | 100 | 15 |
| Asn3 | 11 | 22 | 10 | 100 |

Tables 8 and 9 demonstrate that each variant is an effective immunogen, but in general there is only modest cross-reactivity between variants. The best cross E. Consequences of N-terminal Immunogen Extension on Immunological Conservation and Cross-reactivity Reviewing the Epitope I sequences studied above, the major variation in the Glu-Pro- extension is the occurrence of an Asp for Glu substitution in 9% of sequences. However, as shown in Table 12, antibodies to Glu containing peptides are substantially cross-reactive with the corresponding Asp containing peptide, and vice-versa.

TABLE 12

| Immunogens | Detector Peptides (Titer) | | |
|---|---|---|---|
| | Met-Glu-Pro-Val-Asp-Pro-Arg-Leu-Glu-Pro (amino acids 1–10 of SEQ ID NO: 1) | Met-Asp-Pro-Val-Asp-Pro-Arg-Leu-Glu-Pro (SEQ ID NO: 103) | Val-Asp-Pro-Arg-Leu-Glu-Pro (amino acids 4–10 of SEQ ID NO: 1) |
| Met-Glu-Pro-Val-Asp-Pro-Arg-Leu-Glu-Pro-Trp-Lys (amino acids 1–12 of SEQ ID NO: 1) | 82,000 | 67,000 | 38,000 |
| Met-Asp-Pro-Val-Asp-Pro-Arg-Leu-Glu-Pro-Trp-Lys (SEQ ID NO: 104) | 50,000 | 75,000 | 38,000 |

Other than the variation between Glu and Asp there were only 7 other variants at these two positions (5 Lys/Glu and 2 Leu-Pro substitutions), bringing the immunological conservation of the enlarged Epitope I in B subtype HIV-1 Tat proteins to 95%. For the 18 non B subtype sequences only 16 contained sequence corresponding to the Glu-Pro extension and, apart from Glu/Asp variation, all were Glu-Pro or Asp-Pro except for two F subtype sequences (Glu-Leu), yielding an immunological conservation of 88%. Thus immunization with peptides with extended N-terminal sequence still provides a high incidence of immunoreactivity with a broad sample of known HIV-1 Tat protein sequences.

EXAMPLE 3

Defining an Antibody Binding Amino Acid Sequence (Epitope II) within the Linear 18 Amino Acid Sequence Following $CYS_{37}$ of HIV-1 Tat Protein A peptide corresponding to amino acids 38–55 of SEQ ID NO: 1 illustrated in FIG. 1 was synthesized as described in Example 1. Using the methods described in Example 1, a low titer antibody response in rabbits was detected and Table 28 summarizes studies defining the sequence involved in this antibody binding. The geometric mean titer (GMT) is reported as percentage of self-titer.

TABLE 13

Antiserum to SEQ ID NO: 105:
Phe-Ile-Thr-Lys-Gly-Leu-Gly-Ile-Ser-Tyr-Gly-Arg-Lys-Lys-Arg-Arg-Gln-Arg

| Detector Peptides | GMT (% self titer) | SEQ ID NO. |
|---|---|---|
| Phe-Ile-Thr-Lys-Gly-Leu-Gly-Ile-Ser-Tyr-Gly-Arg-Lys-Lys-Arg-Arg-Gln-Arg | 947 (100) | 105 |
| Phe-Ile-Thr-Lys-Gly-Leu-Gly-Ile-Ser- | 1141 (115) | (amino acids 1–15 of SEQ ID NO: 105) |

TABLE 13-continued

Antiserum to SEQ ID NO: 105:
Phe-Ile-Thr-Lys-Gly-Leu-Gly-Ile-Ser-Tyr-Gly-Arg-Lys-Lys-Arg-Arg-Gln-Arg

| Detector Peptides | GMT (% self titer) | SEQ ID NO. |
|---|---|---|
| Tyr-Gly-Arg-Lys-Lys-Arg | | 1–15 of SEQ ID NO: 105) |
| Lys-Gly-Leu-Gly-Ile-Ser-Tyr-Gly-Arg-Lys-Lys-Arg-Arg-Gln-Arg | 895 (95) | (amino acids 41–55 of SEQ ID NO: 1) |
| Leu-Gly-Ile-Ser-Tyr-Gly-Arg-Lys-Lys-Arg-Arg-Gln-Arg | 986 (104) | (amino acids 43–55 of SEQ ID NO: 1) |
| Gly-Ile-Ser-Tyr-Gly-Arg-Lys-Lys-Arg | 428 (47) | (amino acids 44–52 of SEQ ID NO: 1) |
| Ile-Ser-Tyr-Gly-Arg-Lys-Lys-Arg | 254 (27) | (amino acids 45–52 of SEQ ID NO: 1) |
| Ser-Tyr-Gly-Arg-Lys-Lys-Arg-Arg-Gln-Arg | 53 (6) | (amino acids 46–55 of SEQ ID NO: 1) |
| Leu-Gly-Ile-Ser-Tyr-Gly-Arg-Lys-Lys | 914 (97) | (amino acids 43–51 of SEQ ID NO: 1) |
| Leu-Gly-Ile-Ser-Tyr-Gly-Arg-Lys | 545 (58) | (amino acids 43–50 of SEQ ID NO: 1) |
| Phe-Ile-Thr-Lys-Gly-Leu-Gly-Ile-Ser-Tyr-Gly-Arg | 129 (14) | (amino acids 1–12 of SEQ ID NO: 105) |

These ELISA results established that the low titer antibodies induced bound to the sequence Leu-Gly-Ile-Ser-Tyr-Gly-Arg-Lys-Lys (amino acids 43–51 of SEQ ID NO: 1). Accordingly, this sequence and the sequence Lys-Gly-Leu-Gly-Ile-Ser-Tyr-Gly-Arg-Lys-Lys (amino acids 41–51 of SEQ ID NO: 1) were synthesized and used to immunize rabbits.

Immunizing with the minimal epitope, Leu-Gly-Ile-Ser-Tyr-Gly-Arg-Lys-Lys (amino acids 43–51 of SEQ ID NO: 1), produced low titer antibodies (GMT 1,000) while, surprisingly, immunization with Lys-Gly-Leu-Gly-Ile-Ser-Tyr-Gly-Arg-Lys-Lys (amino acids 41–51 of SEQ ID NO: 1) induced high titer antibodies (GMT 20,000) to the detector peptide Phe-Ile-Thr-Lys-Gly-Leu-Gly-Ile-Ser-Tyr-Gly-Arg-Lys-Lys-Arg-Arg-Gln-Arg (SEQ ID NO: 105).

The variation of sequence occurring within Epitope II was analyzed to enable the design of immunogens that induce antibodies that react with most Epitope II sequences. 441 sequence variations were determined in HIV-1 Tat protein amino acids 41–51 of the common B subtype were obtained, as were 21 from non-B subtypes (7 from subtype A, 4 from subtype C, 7 from subtype D, 2 from subtype F and 1 from subtype U). For the B subtype, 422 of 441 (96%) had the nominal sequence with the exception of an Ala for Gly substitution in 134 (32%). For the non-B subtype sequences 20 of 21 (95%) had the nominal sequence.

The reactivity of antibodies induced by Lys-Gly-Leu-Gly-Ile-Ser-Tyr-Gly-Arg-Lys-Lys (amino acids 41–51 of SEQ ID NO: 1) was studied by titering antiserums to Lys-Gly-Leu-Gly-Ile-Ser-Tyr-Gly-Arg-Lys-Lys (amino acids 41–51 of SEQ ID NO: 1) as follows on the listed detector peptides:

TABLE 14

| Detector Peptides | Titer | SEQ ID NO. |
|---|---|---|
| Phe-Ile-Thr-Lys-Gly-Leu-Gly-Ile-Ser-Tyr-Gly-Arg-Lys-Lys-Arg-Arg-Gln-Arg | 20,000 | 105 |
| Lys-Gly-Leu-Gly-Ile-Ser-Tyr-Gly-Arg-Lys-Lys-Arg-Arg-Gln-Arg | 18,000 | (amino acids 4–18 of SEQ ID NO: 105) |
| Lys-Ala-Leu-Gly-Ile-Ser-Tyr-Gly-Arg-Lys-Lys | 20,000 | 106 |
| Leu-Gly-Ile-Ser-Tyr-Gly-Arg-Lys-Lys | 19,000 | (amino acids 3–11 of SEQ ID NO: 106) |

These data show that there is full immunological cross reactivity with the Ala variant and that the antibody response to Lys-Gly-Leu-Gly-Ile-Ser-Tyr-Gly-Arg-Lys-Lys (amino acids 41–51 of SEQ ID NO: 1) remains directed to the previously identified epitope Leu-Gly-Ile-Ser-Tyr-Gly-Arg-Lys-Lys (amino acids 43–51 of SEQ ID NO: 1). Thus immunization with Lys-Gly-Leu-Gly-Ile-Ser-Tyr-Gly-Arg-Lys-Lys (amino acids 41–51 of SEQ ID NO: 1) induces high titer antibodies which react with greater than 96% of known HIV-1 Tat proteins.

EXAMPLE 4

Immunological Studies on Minimal Tat Protein Amino Acid Sequences Necessary for Binding to Antibody for Epitope III in HIV-1 Tat Protein A peptide was synthesized which corresponded to amino acids 53–62 of SEQ ID NO: 1 illustrated in FIG. 1 as described below. The sequence is the most frequent sequence representations at these positions in 31 Tat protein sequences of the common B subtype reported in the NIAID HIV database. The sequence was chosen as a second putative immunogen.

A. Peptide Synthesis-Immunizing Peptides

The amino acid sequences of the immunogen, -Arg-Gln-Arg-Arg-Arg-Ala-Pro-Gln-Asp-Ser- (SEQ ID NO: 29) was synthesized as described in Example 1 for Epitope I. The experiments for which data is reported are represented in Tables 15–16 below. Immunizing peptides were generally purified to greater than 95% purity by reverse phase HPLC, and purity was further confirmed by mass spectometry (MS). Immunizing peptides were covalently coupled to diphtheria toxoid (DT) carrier protein via the cysteinyl side chain as described for Epitope I in Example 1A.

B. Peptide Synthesis-Detector Peptides

Peptides corresponding to the amino acid sequence of the immunogen peptide were synthesized by the method of Geysen, cited above, for use in ELISA assays for detection of reactivity and cross-reactivity. Additional peptides with N- and C-terminal truncations were also synthesized. For most of the experiments reported below in Table 15, detector peptides had an N-terminal -Ser-Gly-Ser-Gly- (SEQ ID NO: 30) added, with biotinylation of the new N-terminus, and the C-terminal remained a free acid. These detector peptides had a purity exceeding 70% by mass spectometry and were not purified further.

C. Immunization of Rabbits

The peptide conjugates were taken up in purified water and emulsified 1:1 with CFA or IFA as described in Example 1C. Total volume per rabbit was 1 ml, and this contained 100 μg of peptide coupled to DT. Two rabbits were used for the immunizing peptide, with the initial intramuscular (IM) injection with conjugate in CFA and a subsequent IM boost at 2 weeks with conjugate in IFA. A pre-bleed was drawn before the first injection and larger bleeds were taken 3 and 5 weeks after the booster injection.

D. ELISA Determination of Binding of Antiserums to Biotinylated Peptides

These assays were performed as described by H. M. Geysen et al., Proc. Natl. Acad. Sci. USA, 81:3998 (1983) and as described in Example 1D for Epitope I. From the results of Table 15, the definition of another antibody binding region of HIV-1 Tat, referred to herein as Epitope III, is -Arg-Arg-Ala-Pro-Gln-Asp-Ser- (SEQ ID NO: 19).

E. HIV-1 Tat Epitope III Minimal Sequence Analysis

The following experiment was performed using as the immunizing peptide sequence: Arg-Gln-Arg-Arg-Arg-Ala-Pro-Gln-Asp-Ser-NH$_2$ (SEQ ID NO:29). The results in the following Table 15 illustrate that the minimal sequence of Epitope III with maximal binding of antibody is Arg-Arg-Ala-Pro-Gln-Asp-Ser (SEQ ID NO: 19). N-terminal or C-terminal extensions of the detector peptides do not produce significantly different binding. The truncation of N-terminal Arg leads to a modest reduction of binding titer, while truncation of the next N-termninal Arg or the C-terminal Ser lead to almost complete loss of specific binding, indicating that Arg-Ala-Pro-Gln-Asp-Ser (amino acids 57–62 of SEQ ID NO: 1) are the most important amino acids to create interactions with specific antibody (See FIG. 4). GMT is reported as % GMT on detector peptide containing the immunogen sequence.

TABLE 15

| N Term | Detector Sequences | C Term | % binding | SEQ ID # |
|---|---|---|---|---|
| N + 3 | Arg-Gln-Arg-Arg-Arg-Ala-Pro-Gln-Asp-Ser-OH | C0 | 100 | (amino acids 53–62 of SEQ ID NO: 1) |
| N + 2 | Gln-Arg-Arg-Arg-Ala-Pro-Gln-Asp-Ser-OH | C0 | 94 | (amino acids 54–62 of SEQ ID NO: 1) |
| N + 1 | Arg-Arg-Arg-Ala-Pro-Gln-Asp-Ser-OH | C0 | 93 | (amino acids 55–62 of SEQ ID NO: 1) |
| N0 | Arg-Arg-Ala-Pro-Gln-Asp-Ser-OH | C0 | 105 | (amino acids 56–62 of SEQ ID NO: 1) |
| N0 | Arg-Arg-Ala-Pro-Gln-Asp-Ser-Gln-Thr-His-Gln-OH | C + 4 | 107 | (amino acids 56–66 of SEQ ID NO: 1) |
| N − 1 | Arg-Ala-Pro-Gln-Asp-Ser-OH | C0 | 56 | (amino acids 57–62 of SEQ ID NO: 1) |
| N − 2 | Ala-Pro-Gln-Asp-Ser-OH | C0 | 3 | (amino acids 58–62 of SEQ ID NO: 1) |
| N + 3 | Arg-Gln-Arg-Arg-Arg-Ala-Pro-Gln-Asp-OH | C − 1 | 7 | (amino acids 53–61 of SEQ ID NO: 1) |
| N + 3 | Arg-Gln-Arg-Arg-Arg-Ala-Pro-Gln-OH | C − 2 | 4 | (amino acids 53–60 of SEQ ID NO: 1) |

F. HIV-1 Tat Epitope III-Effects of Immunogen on Antibody Titers

Every instance of C-terminal extension results in loss of immunogenicity and lowered titers. In contrast, N terminal extension up to a point enhances immunogenicity, with maximal titers being obtained with Gln-Arg-Arg-Arg-Ala-Pro-Gln-Asp-Ser (amino acids 54–62 of SEQ ID NO: 1) and a drop in immunogenicity occurring with Arg-Arg-Gln-Arg-Arg-Arg-Ala-Pro-Gln-Asp-Ser- (amino acids 52–62 of SEQ ID NO: 1) as the immunogen. GMT on Arg-Gln-Arg-Arg-Arg-Ala-Pro-Gln-Asp-Ser- (amino acids 53–62 of SEQ ID NO: 1) is reported in Table 16 as % of GMT of antiserums to this peptide on this detector peptide.

TABLE 16

| N Term | Immunogen Sequence | C Term | % binding | SEQ ID # |
|---|---|---|---|---|
| N + 3 | Arg-Gln-Arg-Arg-Ala-Pro-Gln-Asp-Ser-NH₂ | C0 | 100 | 107 |
| N + 1 | Gly-Arg-Arg-Ala-Pro-Gln-Asp-Ser-NH₂ | C0 | 11 | 108 |
| N0 | Arg-Arg-Ala-Pro-Gln-Asp-Ser-Gln-Thr-His-Gln-NH₂ | C + 4 | 3 | 109 |
| N + 2 | Gln-Arg-Arg-Arg-Ala-Pro-Gln-Asp-Ser-OH | C0 | 136 | (amino acids 54–62 of SEQ ID NO: 1) |
| N + 3 | Arg-Gln-Arg-Arg-Arg-Ala-Pro-Gln-Asp-Ser-Gln-Thr-OH | C + 2 | 9 | (amino acids 53–64 of SEQ ID NO: 1) |
| N + 3 | Arg-Gln-Arg-Arg-Arg-Ala-Pro-Gln-Asp-Ser-Gln-Thr-His-Gln-OH | C + 4 | 28 | (amino acids 53–66 of SEQ ID NO: 1) |
| N + 4 | Arg-Arg-Gln-Arg-Arg-Arg-Ala-Pro-Gln-Asp-Ser-OH | C0 | 3 | (amino acids 52–62 of SEQ ID NO: 1) |

EXAMPLE 5

Sequence Variations in Epitope III of HIV-1 Tat Protein and Immunological Cross-reactivities of Antiserums to these Sequences Variations in the sequence of Tat protein AA 56–72 were analyzed in sequences available in HUMAN RETROVIRUSES and AIDS 1996, (cited above) and additional sequences (GenBank), as described in Example 4.

A. Variations in Epitope III Sequences 482 sequences of Epitope III of the common B subtype of HIV-1 were available for analysis. The most frequent sequence found conformed to the formula -Arg-Arg-X-Pro-Gln-Y-Ser- (SEQ ID NO: 110), where X is Ala, Pro, Ser, or Gln, and Y is Asp, Asn, Gly or Ser. This sequence type, which appears immunologically cross-reactive (see below), was found in 292 of 482 (61%) of available Tat sequences.

Other sequence variants occurred in lower incidence and these included those listed in Table 17 below.

TABLE 17

| SEQUENCES | # (%) of Tat Sequences | SEQ ID NO. |
|---|---|---|
| -Arg-Arg-Ala-Pro-Pro-Asp-Ser- | 20 (4%) | 20 |
| -Arg-Arg-Ala-Pro-Pro-Asp-Asn- | 21 (4%) | 50 |
| -Arg-Arg-Ala-His-Gln-Asp-Ser- | 20 (4%) | 21 |
| -Arg-Arg-Ala-His-Gln-Asn-Ser- | 17 (3.5%) | 22 |
| -Arg-Arg-Ala-Pro-Gln-Gly-Asn- | 10 (2%) | 51 |
| -Arg-Gly-Ala-Pro-Gln-Asp-Ser- | 9 (2%) | 25 |
| -Arg-Arg-Ala-Pro-Glu-Asp-Ser- | 8 (2%) | 26 |
| -Arg-Arg-Ala-Ser-Gln-Asp-Ser- | 8 (2%) | 27 |

TABLE 17-continued

| SEQUENCES | # (%) of Tat Sequences | SEQ ID NO. |
|---|---|---|
| -Arg-Arg-Pro-Pro-Gln-Asp-Asn- | 9 (2%) | 23 |
| -Arg-Arg-Ala-Pro-Gln-Asp-Arg- | 8 (2%) | 24 |

Together these sequences account for 85% of Epitope III variants, with the balance comprised of a large number of low incidence variations.

Epitope III sequences were only available from 18 examples of HIV-1 non-B subtypes. Unlike Epitope I, they showed divergence from the B subtype sequences and optionally a larger number of sequences can be selected for inclusion into the composition of this invention, if additional non-B subtype Epitope III sequences are determined and are desirable in an immunogenic composition of this invention.

B. Assessment of Immunological Reactivity and Cross Reactivity of Selected Epitope III Sequences Immunizing and detector sequences were synthesized, as described in Example 1, for the sequences in Table 18. Rabbits were immunized and antiserums were tested by ELISA, as described in Example 4, for reactivity and cross-reactivity. The various antiserums and detector peptides were utilized to determine immunogenicity of the various sequences and the extent of immunological cross reactivity. The incidence and immunological reactivity of Epitope III sequences of the formula -Arg-Arg-X-Pro-Gln-Y-Ser- (SEQ ID NO: 10) (see above) are shown in Table 18. In Table 18 below, percent cross-reactivity was measured with antiserum to Cys-Arg-Gln-Arg-Arg-Arg-Ala-Pro-Gln-Asp-Ser- (SEQ ID NO: 74), self titer =46,115. The results of Table 18 demonstrate that immunization with -Arg-Gln-Arg-Arg-Arg-Ala-Pro-Gin-Asp-Ser- (SEQ ID NO: 29) should provide effective cross-presented in 61% of HIV-1 strains.

TABLE 18

| Epitope III Sequence | # per 482 sequences | % Cross-reactivity | SEQ ID NO. |
|---|---|---|---|
| -Arg-Arg-Ala-Pro-Gln-Asp-Ser- | 93 | 100 | 19 |
| -Arg-Arg-Pro-Pro-Gln-Asp-Ser- | 50 | 111 | 75 |
| -Arg-Arg-Pro-Pro-Gln-Asn-Ser- | 41 | 96 | 76 |
| -Arg-Arg-Pro-Pro-Gln-Gly-Ser- | 37 | 97 | 77 |
| -Arg-Arg-Ser-Pro-Gln-Asp-Ser- | 19 | 93 | 73 |
| -Arg-Arg-Thr-Pro-Gln-Gly-Ser- | 14 | 56 | 68 |
| -Arg-Arg-Ala-Pro-Gln-Gly-Ser- | 9 | 87 | 69 |
| -Arg-Arg-Thr-Pro-Gln-Asp-Ser- | 7 | 116 | 70 |
| -Arg-Arg-Ala-Pro-Gln-Asn-Ser- | 5 | 128 | 72 |
| -Arg-Arg-Ser-Pro-Gln-Asp-Ser- | 4 | 110 | 73 |
| -Arg-Arg-Ser-Pro-Gln-Asn-Ser- | 2 | 142 | 78 |
| -Arg-Arg-Ala-Pro-Gln-Ser-Ser- | 1 | 97 | 79 |
| -Arg-Arg-Ser-Pro-Gln-Gly-Ser- | 1 | 78 | 80 |
| -Arg-Arg-Thr-Pro-Gln-Asn-Ser- | 1 | 43 | 81 |
| | 292/482 (61%) | | |

Immunization with -Arg-Arg-Ala-Pro-Pro-Asp-Asn- (SEQ ID NO: 50) and -Arg-Arg-Ala-Pro-Pro-Asp-Ser- (SEQ ID NO: 20) yielded antibodies that cross-reacted with both detector peptides, as shown in Table 19. Thus, inclusion of either sequence in an immunizing composition of this invention provides antibodies against Tat protein Epitope III variants in a further 41/482 (8.5%) of HIV-1 strains.

Immunization with -Arg-Gln-Arg-Arg-Arg-Ala-His-Gln-Asn-Ser- (SEQ ID NO: 52) (20/482 (4%)) induced antibodies that gave a self titer of 209,286 and a cross-reactivity of 5,356 (2.5%) with -Arg-Arg-Ala-His-Gln-Asp-Ser- (SEQ ID NO: 21) (17/482 (3.5%)). Thus inclusion of this sequence in an immunogen covers an additional 27/482 (7.5%) of HIV-1 strains.

Thus, immunization with three Epitope III variants, -Arg-Arg-Ala-Pro-Gln-Asp-Ser- (SEQ ID NO: 19), -Arg-Arg-Ala-Pro-Pro-Asp-Asn- (SEQ ID NO: 50), and -Arg-Arg-Ala-His-Gln-Asn-Ser- (SEQ ID NO: 22), provides antibodies reactive with the Tat proteins of 77% of HIV-1 strains.

TABLE 19

| Anti- | Detector peptides ELISA GMT | |
|---|---|---|
| serum to: | -Arg-Arg-Ala-Pro-Pro-Asp-Asn- (SEQ ID NO: 50) | -Arg-Arg-Ala-Pro-Pro-Asp-Ser- (SEQ ID NO: 20) |
| SEQ ID NO: 50 | 11,056 | 12,230 |
| SEQ ID NO: 20 | 9,340 | 7,865 |

EXAMPLE 6

Immunological Studies on Minimal Tat Protein Amino Acid Sequences Necessary for Binding to Antibody for Epitope IV in HIV-1 Tat Protein A publication by McPhee at al, FEBS Letters 233:393 (1988) suggested that some serums of HIV-1 infected subjects reacted with a synthetic peptide Ser-Gln-Thr-His-Gln-Val-Ser-Leu-Ser-Lys-Gln-Pro-Cys (SEQ ID NO: 111), erroneously reported as amino acids 71–83 of HIV-1 Tat protein (the correct positions are amino acids 61–73). The inventor therefore immunized mice with the synthetic peptide -Ser-Gln-Thr-His-Gln-Val-Ser-Leu-Ser-Lys-Gln-Pro (SEQ ID NO: 112) and determined that antibodies reactive with this peptide were generated, with a geometric mean titer of 26,517.

To determine minimal epitope size, a series of truncated peptides were synthesized and used as detector peptides to determine minimal sequence length requirements for binding. Table 20 reports the detector peptides and percent binding, determined as described in Example 1 for Epitope I.

TABLE 20

| Detector Peptides | % Binding | SEQ ID NO |
|---|---|---|
| -Ser-Gln-Thr-His-Gln-Val-Ser-Leu-Ser-Lys-Gln-Pro-(GMT 26,517) | 100 | 112 |
| -Gln-Thr-His-Gln-Val-Ser-Leu-Ser-Lys-Gln-Pro- | 63 | (amino acids 2–12 of SEQ ID NO: 112) |
| -Thr-His-Gln-Val-Ser-Leu-Ser-Lys-Gln-Pro- | 42 | (amino acids 3–12 of SEQ ID NO: 112) |
| -His-Gln-Val-Ser-Leu-Ser-Lys-Gln-Pro- | 16 | (amino acids 4–12 of SEQ ID NO: 112) |
| -Gln-Val-Ser-Leu-Ser-Lys-Gln-Pro- | 5 | (amino acids 5–12 of SEQ ID NO: 112) |
| -Ser-Gln-Thr-His-Gln-Val-Ser-Leu-Ser-Lys-Gln- | 15 | (amino acids 1–11 of SEQ ID NO: 112) |
| -Ser-Gln-Thr-His-Gln-Val-Ser-Leu-Ser-Lys- | 3 | (amino acids 1–10 of SEQ ID NO: 112) |

From these data, it is clear that all 12 amino acids are necessary for full binding to Epitope IV, although the contribution of amino acids in positions 1 and 2 are not major.

The following determinations were made about sequence variations in Epitope IV and immunological cross-reactivies of antiserums, following the procedures described above for Epitopes I, II and III. 444 examples of this sequence region were available in the data bases. The most common variations were Asn for Thr at position 3 and Ala for Val at position 6. Reactivities of the antiserums to the nominal peptide to detector peptides corresponding to these sequences were studied as described above, and the results of percent binding reported in Table 21 below.

TABLE 21

| Detector Peptides | % Binding | SEQ ID NO. |
|---|---|---|
| -Ser-Gln-Thr-His-Gln-Val-Ser-Leu-Ser-Lys-Gln-Pro-(GMT 26,517) | 100 | 112 |
| -Ser-Gln-Asn-His-Gln-Val-Ser-Leu-Ser-Lys-Gln-Pro- | 85 | 113 |
| -Ser-Gln-Thr-His-Gln-Ala-Ser-Leu-Ser-Lys-Gln-Pro- | 17 | 114 |

Thus amino acid position 3 substitution from Thr to Asn does not materially affect antibody binding, whereas an Ala for Val substitution at amino acid position 6 is essentially non cross-reactive. In the 444 examples of HIV-1 Tat proteins sequenced in this region 282/444 (64%) had sequences that were similar to the nominal sequence. Disregarding amino acid 3 variations between Thr and Asn, 199/444 (45%) had Val as amino acid 6 and 83/444 (19%) had Ala as amino acid 6. In contrast to the poor cross-reactivity of Ala6 peptides with antisera to the Val6 immunogen, antisera to Ala6 peptide gave titers of 26,000 on the Ala6 peptide, and 32,000 on the Val6 peptide, demonstrating complete cross-reactivity.

Thus immunization with proteins containing the amino acid sequence -Ser-Gln-Thr-His-Gln-Ala-Ser-Leu-Ser-Lys-Gln-Pro- (SEQ ID NO: 114) provokes antibodies reactive with 64% of variant HIV-1 Tat proteins.

EXAMPLE 7

Construction of a Synthetic Gene of the Invention

A synthetic gene was constructed that incorporated in frame eight Epitope I variants (including the four primary immunogens of the invention) and thirteen Epitope III variants, these constituting all the variant Epitope I and Epitope III sequences found in the Tat protein sequences of 31 HIV-1 B subtype strains reported in the 1996 HUMAN RETROVIRUSES and AIDS compilation, cited above. These included amino acids 4–16 for Epitope I and 53–62 for Epitope III, using the numbering of SEQ ID NO: 1 illustrated in FIG. 1. The epitope sequences were separated by dipeptide spacers containing Gly and/or Ser residues.

The sequence of this one exemplary gene of this invention is shown in FIGS. 2A–2C (SEQ ID NOS: 2 and 3). The gene was assembled as described in W. P. C. Stemmer et al., Gene, 164:49 (1995). Briefly, eleven top strand 60-mer oligonucleotides (oligos) and eleven bottom strand oligos with 20 nucleotide (nt) overlaps were synthesized along with two end 50-mers. The twenty-two 60-mers were incubated together under hybridizing conditions and polymerase chain reaction (PCR) was used to fill in the sequence and amplify it. The end 50-mers were then added and the assembly completed by PCR, with isolation of the full length gene on agarose gel.

The gene was sequenced and found to have the correct sequence within the actual epitopes, with the exception of an Ala to Thr substitution at position 136 (see FIGS. 2A–2C).

This was accepted since this change does not affect antibody binding of Epitope III (see Example 4).

This gene was then excised with restriction enzymes and inserted into the expression vector pBAD (L-M. Guzman et al., J. Bacteriol, 177:4121 (1950)) containing, in frame, the sequence for green fluorescent protein (GFP) (A. Crameri et al., Nature Biotech, 14:315 (1996)). TG1 *E. coli* were transfected and green-fluorescent colonies were isolated.

The isolated colonies were grown and expression was induced. Protein from each of three colonies had fluorescent bands on Western blotting with the expected molecular size (i.e., twice that of GFP alone). The resulting protein was soluble and was purified by nickel column affinity purification utilizing a hexa-histidyl that had been incorporated in the sequence.

Yield was approximately 1 mg protein per liter of supernatant after double affinity purification to yield >90% purity.

EXAMPLE 8

Immunological Characterization of the Recombinant Fusion Protein Expressing HIV-1 Tat Protein Epitope Variants A. Reactivity of Fusion Protein with Rabbit Antiserums to Epitope I and 2 Variants.

Rabbit antiserums generated to synthetic peptides corresponding to the four primary Epitope I sequences and four Epitope III sequences (see below) were tested by ELISA, using the methodology described in Examples 1 and 4, except that the plates were initially directly coated with a 100 $\mu$g/ml solution of antiserums with the fusion protein.

TABLE 22

| Antiserum to: | Titers on fusion protein | SEQ ID NOS |
|---|---|---|
| -Val-Asp-Pro-Arg-Leu-Glu-Pro-Trp-Lys-His-Pro Gly-Ser- | >>8000 | 28 |
| -Val-Asp-Pro-Asn-Leu-Glu-Pro-Trp-Lys-His-Pro-Gly-Ser- | >>8000 | 47 |
| -Val-Asp-Pro-Lys-Leu-Glu-Pro-Trp-Lys-His-Pro-Gly-Ser- | >>8000 | 45 |
| -Val-Asp-Pro-Ser-Leu-Glu-Pro-Trp-Lys-His-Pro-Gly-Ser- | >8000 | 46 |
| -Arg-Gln-Arg-Arg-Arg-Ala-Pro-Gln-Asp-Ser- | 7000 | 29 |
| -Arg-Gln-Arg-Arg-Arg-Ala-His-Gln-Asn-Ser- | >>8000 | 52 |
| -Arg-Gln-Arg-Arg-Arg-Pro-Pro-Gln-Asp-Ser- | >8000 | 53 |
| -Arg-Gln-Arg-Gln-Arg-Ala-Pro-Asp-Ser-Ser- | 8000 | 82 |

These data show that the variant epitope sequences, expressed as a linear recombinant fusion protein, are expressed in a conformation recognizable by antibodies to the corresponding synthetic peptides.

B. Immunization of Mice with the Fusion Protein

Three mice were immunized with 10 $\mu$g each of an aqueous solution of the fusion protein of Example 7 emulsified with an equal volume of Freund's complete adjuvant, given intraperitoneally. Two weeks later they were similarly boosted, except that Freund's incomplete adjuvant was used. Serums were obtained three weeks later.

C. ELISA Testing of Antiserums to the Fusion Protein with Synthetic Peptides Corresponding to the Epitope Variants Incorporated in the Fusion Protein ELISA testing was performed as described in Example 1 except that horseradish peroxidase conjugated anti-mouse immunoglobulin was used to detect antibody binding. The results are summarized in Table 23 below. These data demonstrate that both Epitope I and Epitope III sequences are expressed in the linear fusion protein, and react with antibodies to the synthetic sequences (see above). Antibodies to Epitope I were detectably induced by the recombinant fusion protein under the conditions of this experiment in mice. The failure of Epitope III sequences expressed within this linear peptide is in keeping with the findings with synthetic peptides, wherein C-terminal extension of the immunogen diminishes the resulting antibody titer (see Example 4).

TABLE 23

| Detector peptides | Titer with antiserum to fusion protein | SEQ ID NO |
|---|---|---|
| -Val-Asp-Pro-Arg-Leu-Glu-Pro-Trp-Lys-His-Pro-Gly-Ser | 2218 | 28 |
| -Val-Asp-Pro-Asn-Leu-Glu-Pro-Trp-Lys-His-Pro-Gly-Ser | 3158 | 47 |
| -Val-Asp-Pro-Lys-Leu-Glu-Pro-Trp-Lys-His-Pro-Gly-Ser | 2440 | 45 |
| -Val-Asp-Pro-Ser-Leu-Glu-Pro-Trp-Lys-His-Pro-Gly-Ser | 3031 | 46 |
| -Val-Asn-Pro-Ser-Leu-Glu-Pro-Trp-Lys-His-Pro-Gly-Ser | 3718 | 48 |
| -Val-Asp-His-Arg-Leu-Glu-Pro-Trp-Lys-His-Pro-Gly-Ser | 3223 | 49 |
| -Arg-Gln-Arg-Arg-Arg-Ala-Pro-Gln-Asp-Ser- | background | 29 |
| -Arg-Gln-Arg-Arg-Arg-Ala-His-Gln-Asn-Ser- | " | 52 |
| -Arg-Gln-Arg-Arg-Arg-Pro-Pro-Gln-Asp-Ser- | " | 53 |
| -Arg-Gln-Arg-Gln-Arg-Ala-Pro-Asp-Ser-Ser- | " | 82 |
| -Arg-Gln-Arg-Arg-Arg-Ala-Pro-Glu-Asp-Ser- | " | 83 |
| -Arg-Gln-Arg-Arg-Arg-Pro-Pro-Gln-Gly-Ser- | " | 59 |
| -Arg-Gln-Arg-Arg-Gly-Pro-Pro-Gln-Gly-Ser- | " | 60 |
| -Arg-Gln-Arg-Arg-Arg-Pro-Pro-Gln-Asn-Ser- | " | 61 |
| -Arg-Gln-Arg-Arg-Arg-Ser-Pro-Gln-Asp-Ser- | " | 62 |
| -Arg-Gln-Arg-Arg-Arg-Ser-Pro-Gln-Asn-Ser- | " | 63 |
| -Arg-Gln-Arg-Arg-Arg-Thr-Pro-Gln-Ser-Ser- | " | 64 |
| -Arg-Gln-Arg-Arg-Arg-Ala-His-Gln-Asp-Ser- | " | 65 |
| -Arg-Gln-Arg-Arg-Arg-Ala-Pro-Pro-Asp-Ser- | " | 66 |

EXAMPLE 9

Primate Animal Study

A study was conducted in ten juvenile male rhesus macaques to determine if the presence of antibodies to Tat protein, induced by a synthetic peptide of this invention prior to infection with immunodeficiency virus, would attenuate infection and reduce levels of virus in plasma. HIV-1 does not infect monkeys, but a corresponding simian immunodeficiency virus (SIV) does. P. A. Luciw et al., Proc. Natl. Acad. Sci. USA, 92:7490 (1995) constructed an infectious recombinant virus (chimera) of $SIV_{mac239}$ and HIV-$1_{SF33}$ that does infect monkeys, typically causing an acute viremia that peaks around 2 weeks and subsequently subsides by week 8. In this chimeric construct, termed $SHIV_{SF33}$, the SIV nucleotides encoding tat, rev and env (gp160) of $SIV_{mac239}$ have been replaced with the corresponding region of HIV-$1_{SF33}$.

A. Immunization of Monkeys

The monkeys were randomized into two groups.

Each monkey of group 1 (control group) was immunized with 0.4 mg diphtheria toxoid (Commonwealth Scrum Laboratories, Victoria, Australia) with 0.25 mg threonyl muramyl dipeptide (T-MDP) in 0.5 ml water, this being emulsified with 0.5 ml ME75 adjuvant (Chiron Corp, Emeryville Calif.).

Each monkey of group 2 (test group) was immunized with 0.1 mg of the synthetic peptide Cys-Val-Asp-Pro-Asn-Leu-Glu-Pro-Trp-His-Pro-Gly-Ser-amide (SEQ ID NO: 84)

coupled to 0.4 mg diphtheria toxoid (A. C. Lee et al., Mol. Immunol., 17:749 (1980)). The conjugate was dissolved in 0.5 ml water containing 0.25 mg T-MDP and emulsified with 0.5 ml MF75 adjuvant.

Each monkey was immunized at day 0 and day 28 (week 4) with two 0.5 ml intramuscular injections at two distinct sites. The synthetic peptide immunogen contained the B cell Epitope I, Val-Asp-Pro-Asn-Leu-Glu-Pro-Trp-Lys-His-Pro-Gly-Ser- (SEQ ID NO: 115) of the Tat protein of SF33 HIV-1 that is incorporated in the $SHIV_{SF33}$ molecular clone that was used to challenge the monkeys (see above).

B. Testing for Antibodies to Tat Protein

At day 42 (week 6), 2 weeks after the booster injection, serums were drawn and tested by ELISA for binding to Ser-Gly-Ser-Gly-Val-Asp-Pro-Asn-Leu-Glu-Pro-Trp-Lys-His-Pro-Gly-Ser-OH (SEQ ID NO: 85), as described above in Example 1.

The control monkeys had background titers ranging from 25 to 44, while the test group had titers of 1788 to 9588, as shown in Table 24 below.

TABLE 24

| CONTROL GROUP | | TEST GROUP | |
|---|---|---|---|
| Monkey # | Titer | Monkey # | Titer |
| 18782 | 30 | 18759 | 1788 |
| 18785 | 25 | 18789 | 5780 |
| 18786 | 30 | 18790 | 2718 |
| 18859 | 54 | 18863 | 4139 |
| 18908 | 46 | 18945 | 9588 |
| GMT | 35 | GMT | 4068 |

C. Viral Challenge

At day 49 (week 7) after initial immunization, all monkeys were given 1 ml of a 1/1000 dilution of animal titered SHIV $_{SF33}$ stock intravenously (challenge day 0). This corresponded to 50 animal infectious doses$_{50\%}$ (50 $AID_{50}$) or 200 tissue culture infectious doses$_{50\%}$ (200 $TCID_{50}$).

D. Assessment of Infection

Plasma was drawn in EDTA at weeks 2, 4 and 8, and copies of viral RNA per ml of plasma were measured by QR-RT-PCR, using SIV probes for the SIV component of $SHIV_{SF33}$ (A. J. Conrad et al., J. Acq. Imm. Def. Syndrome and Hum. Retrovirol., 10:425 (1995)). The results are summarized as follows in Tables 25 and 26.

TABLE 25

| CONTROLS | | SHIV RNA copies/ml plasma | |
|---|---|---|---|
| Monkey # | 2 weeks | 4 weeks | 8 weeks |
| 18782 | 880,000 | 30,000 | <500 |
| 18785 | 610,000 | 80,000 | <500 |
| 18786 | 500,000 | 50,000 | <500 |
| 18859 | 22,000,000 | 120,000 | <500 |
| 18908 | 20,000,000 | 100,000 | 1,000 |
| GMT | 2,596,851 | 67,869 | |

TABLE 26

| CONTROLS | | SHIV RNA copies/ml plasma | |
|---|---|---|---|
| Monkey # | 2 weeks | 4 weeks | 8 weeks |
| 18759 | 920,000 | 60,000 | <500 |
| 18789 | 950,000 | 50,000 | <500 |
| 18790 | 390,000 | 17,000 | <500 |

TABLE 26-continued

| CONTROLS | | SHIV RNA copies/ml plasma | |
|---|---|---|---|
| Monkey # | 2 weeks | 4 weeks | 8 weeks |
| 18863 | 2,000,000 | 27,000 | <500 |
| 18945 | 330,000 | 65,000 | 500 |
| GMT | 742,034 | 38,938 | |
| INHIBITION: TEST VERSUS CONTROLS | 71% | | 43% |

As expected, $SHIV_{SF33}$ caused an acute infection, with peak levels of viral RNA at 2 weeks and barely or non-detectable levels by week 8. Monkeys immunized with a synthetic peptide conjugate that induced antibodies to the Tat protein of the challenge $SHIV_{SF33}$ virus had, by comparison with control immunized monkeys, a 71% reduction in peak virus levels in plasma 2 weeks after viral challenge, with a 43% inhibition being still detectable in the subsiding plasma viral levels at 4 weeks. This shows that SHIV multiplication in vivo was inhibited in the presence of antibodies to the Tat protein being utilized by the virus, and suggests that a similar effect would prevail in HIV infected humans.

E. Assessment of Seroconversion

Subjects infected with HIV develop antibodies to virion surface proteins and this is detected by ELISA and used to diagnose infection. Monkey serums were tested prior to virus challenge and 8 weeks after challenge, using the HIVAB®HIV-1/HIV-2(rDNA)EIA (Abbott Labs, IL). All pre-challenge serums were negative and all 8 week post challenge serums were positive. These findings provide additional support for the fact that antibodies to Tat protein do not register in diagnostic assays for HIV seroconversion.

EXAMPLE 10

Primate Animal Study

An additional monkey study was performed using immunization with synthetic peptides coupled to diphtheria toxoid (9 monkeys) or diphtheria toxoid immunized controls (5 monkeys). Initial immunization was with Freund's complete adjuvant, with boosts at 3, 6 and 9 weeks with incomplete Freund's adjuvant. The immunizing peptides were Cys-Val-Asp-Pro-Asn-Leu-Glu-Pro-Trp-Lys-His-Pro-Gly-Ser-amide (SEQ ID NO: 116) (Epitope I) and Cys-Arg-Gln-Arg-Arg-Arg-Ala-Pro-Asp-Ser-Ser-Gln-Asn-His-Gln-OH (SEQ ID NO: 117) (Epitope III).

Monkeys were challenged with 50 $AID_{50}$ of SHIV33, as above, 2 weeks after the last boost with immunogen. Geometric mean titers at 11 weeks (time of challenge) in immunized animals were 46,000 for Epitope I and 5,000 for Epitope III.

Geometric mean plasma viral loads at the peak (2 weeks) were 456,000 for the test group and 234,000 for the controls. However, from 4 weeks post challenge on viral loads in the test group dropped significantly below those in the control group (Table 27).

TABLE 27

|  | Week 4 | Week 8 | Week 12 | Week 16 |
|---|---|---|---|---|
| GML Viral load- controls | 17,000 | 900 | 400 | 120 |
| (# negative) | (0/5) | (0/5) | (0/5) | (1/5) |
| GML Viral load - tests | 5,000 | 300 | 8 | 4 |
| (# negative) | (0/9) | (0/9) | (6/9) | (7/9) |
| % inhibition | 71% | 67% | 98% | 97% |

Seroconversion to SIV positive occured at 4–8 weeks. Thus the post seroconversion viral loads (the most significant prognostic marker in HIV-1 infection) were significantly lowered in the presence of antibodies to HIV-1 Tat protein.

In an effort to understand the high peak viral load at 2 weeks in the test group, serums were tested at the time of viral challenge (2 weeks post the last immunization) for TNFα by ELISA. TNFα, which is released during an immune response, activates cells and is known to by-pass the requirement for Tat mediated activation to support HIV-1 proliferation. The inventor determined that whereas serum TNFα was undetectable pre-immunization, it was detected in all Tat immunized monkeys 2 weeks post immunization with a mean level of 7 pg/ml.

It was concluded that the effects of Tat interdiction on the acute infection were masked by the peri-immunization TNFα activation; once this subsided, the Tat immunized group developed significantly lower viral loads, with the majority having undetectable (<100 copies/ml) levels in plasma.

EXAMPLE 11

Method and Kits for Detecting Titers and Specificities of Antibodies Induced by Vaccination To follow the titer and specificities of antibodies induced following immunization with the vaccines of this invention, an assay method may be employed. In one embodiment of such as assay, peptides containing the sequences reported in Table 28 (depending on the composition of the immunizing vaccine) are used to develop kits measuring titers and reactivity patterns of antibodies in vaccinated subjects.

TABLE 28

| Epitope | Sequence | SEQ ID NOS |
|---|---|---|
| I | -Glu-Pro-Val-Asp-Pro-Arg-Leu-Glu-Pro- | (amino acids 2–10 of SEQ ID NO: 1) |
| I | -Glu-Pro-Val-Asp-Pro-Lys-Leu-Glu-Pro- | 118 |
| I | -Glu-Pro-Val-Asp-Pro-Ser-Leu-Glu-Pro- | 119 |
| I | -Glu-Pro-Val-Asp-Pro-Asn-Leu-Glu-Pro- | 120 |
| II | -Lys-Gly-Leu-Gly-Ile-Ser-Tyr-Gly-Arg-Lys-Lys- | (amino acids 41–51 of SEQ ID NO: 1) |
| III | -Arg-Arg-Ala-Pro-Pro-Asp-Ser- | (amino acids 266–272 of SEQ ID NO: 3) |
| III | -Arg-Arg-Ala-His-Gln-Asp-Ser- | 121 |
| III | -Arg-Arg-Ala-Pro-Gln-Asp-Ser- | 19 |
| IV | -Ser-Gln-Thr-His-Gln-Val-Ser-Leu-Ser-Lys-Gln-Pro- | 122 |

These peptides are synthesized with Biotin-Ser-Gly-Ser-Gly- (SEQ ID NO: 123) at the N-terminus. Each peptide is coated onto separate avidin coated plates, with a sequence -Ser-Gly-Ser-Gly- (SEQ ID NO: 30) serving as a spacer to ensure that the relevant peptide sequence is external to the biotin binding pocket of avidin. The plates are then incubated with dilutions of test serum, washed, and the antibody binding determined with reagent to human immunoglobulin, e.g., rabbit anti-human immunoglobulin, bound to, e.g., biotin, or directly labeled with enzyme. An avidin-enzyme complex is used to detect the biotin label, or a reagent employed to react with the enzyme and produce a calorimetric signal (R&D kit inserts).

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. An antibody composition comprising at least one antibody which specifically binds to at least two variants of an epitope of an HIV-1 Tat protein, said epitope located within the amino acid sequence R1-Val-Asp-Pro-Y-Leu-Glu-Pro-R2 SEQ ID NO: 36, wherein Y is selected from the group consisting of Arg Lys, Ser and Asn, wherein R1 is a sequence of up to 5 amino acids, wherein R2 is a sequence of up to 14 additional amino acids, and each variant has a different amino acid at Y, and wherein said antibody composition binds to HIV-1 Tat proteins from multiple different HIV-1 strains and subtypes.

2. The composition according to claim 1, comprising a mixture of from one to four different said antibodies, said mixture capable of binding three different Y variants of the epitope defined by said SEQ ID NO: 36.

3. The composition according to claim 1, comprising a mixture of from one to four different said antibodies, said mixture capable of binding four different Y variants of the epitope defined by said SEQ ID NO: 36.

4. The composition according to claim 1, comprising an antibody to an HIV Tat-1 protein that specifically binds to an epitope located within the amino acid sequence -Lys-X-Leu-Gly-Ile-Ser-Tyr-Gly-Arg-Lys-Lys- of SEQ ID NO: 37, wherein said amino acid X is Gly or Ala.

5. The composition according to claim 1, wherein said antibody in said composition is selected from the group consisting of an isolated polyclonal antibody, a monoclonal antibody, a chimeric antibody, a humanized antibody, a human antibody, an antibody produced by screening phage displays, and mixtures thereof.

6. A pharmaceutical composition comprising an antibody composition of claim 1 and a pharmaceutically acceptable carrier.

7. A pharmaceutical composition comprising an antibody composition of claim 2 and a pharmaceutically acceptable carrier.

8. A pharmaceutical composition comprising an antibody composition of claim 3 and a pharmaceutically acceptable carrier.

9. A pharmaceutical composition comprising an antibody composition of claim 4 and a pharmaceutically acceptable carrier.

10. A pharmaceutical composition comprising an antibody composition of claim 5 and a pharmaceutically acceptable carrier.

* * * * *

UNITED STATES PATENT AND TRADEMARK OFFICE
CERTIFICATE OF CORRECTION

PATENT NO. : 7,008,622 B2
APPLICATION NO. : 10/086208
DATED : March 7, 2006
INVENTOR(S) : Goldstein It is certified that error appears in the above-identified patent and that said Letters Patent is hereby corrected as shown below:

Title page, (60) Related U.S. Application Data, replace "5,871,994" with -- 5,891,994 -- ;

Col. 1, line 48, replace "Coomnbs" with -- Coombs -- ;

Col. 2, line 13, replace "JAAM" with -- JAMA -- ;

Col. 2, line 66, replace "polygonal" with -- polyclonal -- ;

Col. 3, line 49, replace "areproduced" with -- are produced -- ;

Col. 3, line 59, replace "lone" with -- one -- ;

Col. 4, line 3, replace "termninal" with -- terminal -- ;

Col. 4, line 25, replace "Gin" with -- Gln -- ;

Col. 4, line 28, replace "Gin" with -- Gln -- ;

Col. 4, line 35, replace "Epitope ID" with -- Epitope III -- ;

Col. 5, line 11, replace "Epitope It" with -- Epitope II -- ;

Col. 9, line 11, Table 1, replace "45,000 (65)" with -- 45,000 (55) -- ;

Col. 10, line 64, replace "NLAID" with -- NIAID -- ;

Col. 11, line 48, replace "Gin" with -- Gln -- ;

Col. 12, line 56, replace "SEQ if)" with -- SEQ ID -- ;

Col. 13, line 66, replace "Lys-Glu-Leu-Gly-Ile-Ser-Tyr-Gly-Arg-Lys-Lys-amide" with -- Lys-Glu-Leu-Gly-Ile-Ser-Tyr-Gly-Arg-Lys-Lys-amide -- ;

Col. 16, line 2, replace "polypeptidelpeptide" with -- polypetide/peptide -- ;

Col. 16, line 22, replace "11478-11492" with -- 11478-11482 -- ;

Col. 18, line 37, replace "I,IV" with -- III, IV -- ;

Col. 19, Line 34, replace "polyrations," with -- polycations -- ;

UNITED STATES PATENT AND TRADEMARK OFFICE
CERTIFICATE OF CORRECTION

PATENT NO. : 7,008,622 B2
APPLICATION NO. : 10/086208
DATED : March 7, 2006
INVENTOR(S) : Goldstein It is certified that error appears in the above-identified patent and that said Letters Patent is hereby corrected as shown below:

Col. 19, line 60, replace "990%," with -- 90%, -- ;

Col. 29, line 44, Table 8, delete "Pro-Gly-Ser-"

Col. 36, lines 35-36, replace "cross-presented in 61% of HIV-1 strains" with -- cross-reactivity with most of these variants, represented in 61% of HIV-1 stains --

Col. 40, line 63, replace "ME75" with -- MF75 -- ;

Col. 44, line 34, replace "calori-" with -- colori- -- ;

Signed and Sealed this

Fifth Day of September, 2006

JON W. DUDAS
*Director of the United States Patent and Trademark Office*

SEQUENCE LISTING (1) GENERAL INFORMATION:

(iii) NUMBER OF SEQUENCES: 124

(2) INFORMATION FOR SEQ ID NO: 1:

(i) SEQUENCE CHARACTERISTICS:
      (A) LENGTH: 72 amino acids
      (B) TYPE: amino acid
      (C) STRANDEDNESS: <Unknown>
      (D) TOPOLOGY: linear (ii) MOLECULE TYPE: protein (xi) SEQUENCE DESCRIPTION: SEQ ID NO: 1:

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Thr Thr Lys Gly Leu Gly Ile Ser Tyr Gly
```

```
                35                  40                  45
Arg Lys Lys Arg Arg Gln Arg Arg Ala Pro Gln Asp Ser Gln Thr
    50                  55                  60

His Gln Val Ser Leu Ser Lys Gln
 65                  70

(2) INFORMATION FOR SEQ ID NO: 2:

(i) SEQUENCE CHARACTERISTICS:
        (A) LENGTH: 912 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: join(1..876, 883..912)

(xi) SEQUENCE DESCRIPTION: SEQ ID NO: 2:

GAG CTC TAC AAA TCC GGG GAT CCG GGT GAA GAT CCG CGT TTA GAG CCG         48
Glu Leu Tyr Lys Ser Gly Asp Pro Gly Glu Asp Pro Arg Leu Glu Pro
  1               5                  10                  15

TGG AAA CAC CCG GGT TCT GGT TCT GTT GAC CCT AAC CTT GAA CCT TGG         96
Trp Lys His Pro Gly Ser Gly Ser Val Asp Pro Asn Leu Glu Pro Trp
             20                  25                  30

AAG CAT CCT GGC AGC TCC GGA GTC GAT CCC AAA CTC GAG CCC TGG AAA        144
Lys His Pro Gly Ser Ser Gly Val Asp Pro Lys Leu Glu Pro Trp Lys
         35                  40                  45

CAC CCC GGA AGT TCG GGG GTA GAC CCA TCT CTG GAA CCA TGG AAG CAT        192
His Pro Gly Ser Ser Gly Val Asp Pro Ser Leu Glu Pro Trp Lys His
     50                  55                  60

CCA GGG AGT GGT AGC GTG AAT CCG TCA TTA GAG CCG TGG AAA CAC CCG        240
Pro Gly Ser Gly Ser Val Asn Pro Ser Leu Glu Pro Trp Lys His Pro
 65                  70                  75                  80

GGT TCA TCT GGA GTT GAT CCT CGC TTG GAA CCT TGG GAG CAT CCT GGT        288
Gly Ser Ser Gly Val Asp Pro Arg Leu Glu Pro Trp Glu His Pro Gly
                 85                  90                  95

TCG TCC GGT GTA GAC CCC CGA CTT GAG CCC TGG AAT CAC CTC GGG AGT        336
Ser Ser Gly Val Asp Pro Arg Leu Glu Pro Trp Asn His Leu Gly Ser
            100                 105                 110

TCA GGC GTA GAT CAT CGG CTC GAA CCA TGG AAA CAT CCA GGT TCT GGA        384
Ser Gly Val Asp His Arg Leu Glu Pro Trp Lys His Pro Gly Ser Gly
        115                 120                 125

GAT CTG CGC CAG CGG CGA CGT ACT CCT CAG GAT TCT GGA TCT CGA CAA        432
Asp Leu Arg Gln Arg Arg Arg Thr Pro Gln Asp Ser Gly Ser Arg Gln
    130                 135                 140

CGT CGG CGC CCT CCC CAA GAC TCC TCA GGA CGG CAG CGC CGA CGA CCC        480
Arg Arg Arg Pro Pro Gln Asp Ser Ser Gly Arg Gln Arg Arg Arg Pro
145                 150                 155                 160

CCA CAG GGT TCA GGT TCA CGT CAA CGA CGC GGT CCA CCC CAA GGC TCG        528
Pro Gln Gly Ser Gly Ser Arg Gln Arg Arg Gly Pro Pro Gln Gly Ser
                165                 170                 175

GGT TCG CGC CAG CGG CGA CGT CCG CCT CAG AAC TCT AGT GGA CGA CAA        576
Gly Ser Arg Gln Arg Arg Arg Pro Pro Gln Asn Ser Ser Gly Arg Gln
            180                 185                 190

CGT CGG CGC TCT CCC CAA GAT TCC GGC GGG CGG CAG CGC CGT CGA TCA        624
Arg Arg Arg Ser Pro Gln Asp Ser Gly Gly Arg Gln Arg Arg Arg Ser
        195                 200                 205

CCA CAG AAC TCA GGT GGG CGT CAA CGA CGC CGG ACT CCG CAA TCT TCA        672
Pro Gln Asn Ser Gly Gly Arg Gln Arg Arg Arg Thr Pro Gln Ser Ser
```

```
           210                 215                 220
TCC GGC CGC CAG CGG CGA CGT GCC CAT CAG AAT AGC GGC AGC CGA CAA          720
Ser Gly Arg Gln Arg Arg Arg Ala His Gln Asn Ser Gly Ser Arg Gln
225                 230                 235                 240

CGT CGG CGC GCA CAC CAA GAC AGC AGT GGG CGG CAG CGC CGT CGA GCG          768
Arg Arg Arg Ala His Gln Asp Ser Ser Gly Arg Gln Arg Arg Arg Ala
                245                 250                 255

CCT GAA GAT AGT GGT TCT CGT CAA CGA CGC CGG GCT CCC CCT GAC AGC          816
Pro Glu Asp Ser Gly Ser Arg Gln Arg Arg Arg Ala Pro Pro Asp Ser
            260                 265                 270

TCC GGA CGC CAG CGG CAA CGT GCA CCA GAT AGT TCC TCA GGT CAT CAC          864
Ser Gly Arg Gln Arg Gln Arg Ala Pro Asp Ser Ser Ser Gly His His
        275                 280                 285

CAC CAT CAT CAC TAATAA GAA TTC GGA TCC TCT AGA GTC GAC AAG CTT           912
His His His His        Glu Phe Gly Ser Ser Arg Val Asp Lys Leu
    290                     295                 300
```

(2) INFORMATION FOR SEQ ID NO: 3:

(i) SEQUENCE CHARACTERISTICS:
      (A) LENGTH: 302 amino acids
      (B) TYPE: amino acid
      (D) TOPOLOGY: linear (ii) MOLECULE TYPE: protein (xi) SEQUENCE DESCRIPTION: SEQ ID NO: 3:

```
Glu Leu Tyr Lys Ser Gly Asp Pro Gly Glu Asp Pro Arg Leu Glu Pro
1               5                   10                  15

Trp Lys His Pro Gly Ser Gly Ser Val Asp Pro Asn Leu Glu Pro Trp
                20                  25                  30

Lys His Pro Gly Ser Ser Gly Val Asp Pro Lys Leu Glu Pro Trp Lys
            35                  40                  45

His Pro Gly Ser Ser Gly Val Asp Pro Ser Leu Glu Pro Trp Lys His
        50                  55                  60

Pro Gly Ser Gly Ser Val Asn Pro Ser Leu Glu Pro Trp Lys His Pro
65                  70                  75                  80

Gly Ser Ser Gly Val Asp Pro Arg Leu Glu Pro Trp Glu His Pro Gly
                85                  90                  95

Ser Ser Gly Val Asp Pro Arg Leu Glu Pro Trp Asn His Leu Gly Ser
            100                 105                 110

Ser Gly Val Asp His Arg Leu Glu Pro Trp Lys His Pro Gly Ser Gly
        115                 120                 125

Asp Leu Arg Gln Arg Arg Thr Pro Gln Asp Ser Gly Ser Arg Gln
130                 135                 140

Arg Arg Arg Pro Pro Gln Asp Ser Ser Gly Arg Gln Arg Arg Arg Pro
145                 150                 155                 160

Pro Gln Gly Ser Gly Ser Arg Gln Arg Arg Gly Pro Pro Gln Gly Ser
                165                 170                 175

Gly Ser Arg Gln Arg Arg Arg Pro Pro Gln Asn Ser Ser Gly Arg Gln
            180                 185                 190

Arg Arg Arg Ser Pro Gln Asp Ser Gly Gly Arg Gln Arg Arg Arg Ser
        195                 200                 205

Pro Gln Asn Ser Gly Gly Arg Gln Arg Arg Arg Thr Pro Gln Ser Ser
    210                 215                 220

Ser Gly Arg Gln Arg Arg Arg Ala His Gln Asn Ser Gly Ser Arg Gln
225                 230                 235                 240
```

```
Arg Arg Arg Ala His Gln Asp Ser Ser Gly Arg Gln Arg Arg Ala
            245                 250                 255

Pro Glu Asp Ser Gly Ser Arg Gln Arg Arg Ala Pro Pro Asp Ser
            260                 265                 270

Ser Gly Arg Gln Arg Gln Arg Ala Pro Asp Ser Ser Gly His His
            275                 280                 285

His His His His Glu Phe Gly Ser Ser Arg Val Asp Lys Leu
    290                 295                 300

(2) INFORMATION FOR SEQ ID NO: 4:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Arg Lys Lys Arg Arg Gln Arg Arg Arg
1               5

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Gly Arg Gly Asp Ser Pro
1               5

(2) INFORMATION FOR SEQ ID NO: 6:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Val Asp Pro Arg Leu Glu Pro
1               5

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Val Asp Pro Lys Leu Glu Pro
1               5

(2) INFORMATION FOR SEQ ID NO: 8:
```

```
        (i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 8:

Val Asp Pro Ser Leu Glu Pro
1               5

(2) INFORMATION FOR SEQ ID NO: 9:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 9:

Val Asp Pro Asn Leu Glu Pro
1               5

(2) INFORMATION FOR SEQ ID NO: 10:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Binding-site
            (B) LOCATION: 6
            (D) OTHER INFORMATION: /note= "an amide is attached to the
                Ser in position 6"

(xi) SEQUENCE DESCRIPTION: SEQ ID NO: 10:

Trp Lys His Pro Gly Ser
1               5

(2) INFORMATION FOR SEQ ID NO: 11:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 11:

Gly Pro Arg Leu Glu Pro
1               5

(2) INFORMATION FOR SEQ ID NO: 12:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 12:
```

```
Ala Pro Arg Leu Glu Pro
1               5

(2) INFORMATION FOR SEQ ID NO: 13:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

His Pro Arg Leu Glu Pro
1               5

(2) INFORMATION FOR SEQ ID NO: 14:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

Asp Pro Gly Leu Glu Pro
1               5

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:

Asp Pro Arg Ile Glu Pro
1               5

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

Asp Pro Arg Leu Gly Pro
1               5

(2) INFORMATION FOR SEQ ID NO: 17:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide
```

(xi) SEQUENCE DESCRIPTION: SEQ ID NO: 17:

Asp Pro Arg Leu Glu Ala
1               5

(2) INFORMATION FOR SEQ ID NO: 18:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

Asn Pro Ser Leu Glu Pro
1               5

(2) INFORMATION FOR SEQ ID NO: 19:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

Arg Arg Ala Pro Gln Asp Ser
1               5

(2) INFORMATION FOR SEQ ID NO: 20:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 20:

Gln Arg Arg Arg Ala Pro Gln Asp Ser
1               5

(2) INFORMATION FOR SEQ ID NO: 21:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

Gln Arg Arg Arg Ala His Gln Asp Ser
1               5

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

Gln Arg Arg Arg Ala Pro Pro Asp Ser
1               5

(2) INFORMATION FOR SEQ ID NO: 23:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 23:

Arg Arg Pro Pro Gln Asp Asn
1               5

(2) INFORMATION FOR SEQ ID NO: 24:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Arg Arg Ala Pro Gln Asp Arg
1               5

(2) INFORMATION FOR SEQ ID NO: 25:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 25:

Arg Gly Ala Pro Gln Asp Ser
1               5

(2) INFORMATION FOR SEQ ID NO: 26:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 26:

Arg Arg Ala Pro Glu Asp Ser
1               5

(2) INFORMATION FOR SEQ ID NO: 27:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 27:

Arg Arg Ala Ser Gln Asp Ser
1               5

(2) INFORMATION FOR SEQ ID NO: 28:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 13
        (D) OTHER INFORMATION: /note= "Ser in position 13 is
            optionally modified with NH2"

(xi) SEQUENCE DESCRIPTION: SEQ ID NO: 28:

Val Asp Pro Arg Leu Glu Pro Trp Lys His Pro Gly Ser
1               5                   10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Arg Gln Arg Arg Arg Ala Pro Gln Asp Ser
1               5                   10

(2) INFORMATION FOR SEQ ID NO: 30:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Ser Gly Ser Gly
1

(2) INFORMATION FOR SEQ ID NO: 31:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

Val Asp Pro Arg Leu Pro Trp Lys His Pro Gly Ser
1               5                   10

(2) INFORMATION FOR SEQ ID NO: 32:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 32:

Asp Pro Arg Leu Pro Trp Lys His Pro Gly Ser
1               5                   10

(2) INFORMATION FOR SEQ ID NO: 33:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 33:

Val Asp Pro Arg Leu Pro Trp
1               5

(2) INFORMATION FOR SEQ ID NO: 34:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 34:

Val Asp Pro Arg Leu Pro
1               5

(2) INFORMATION FOR SEQ ID NO: 35:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 35:

Val Asp Pro Arg Leu
1               5

(2) INFORMATION FOR SEQ ID NO: 36:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa in the first position
                may be absent, or may be 1-5 aa, which may be optionally
                modified with a lower alkyl or a lower alkanoyl, or Xaa

```
            may be X-Pro, wherein X is Glu or Asp."

(ix) FEATURE:
       (A) NAME/KEY: Modified-site
       (B) LOCATION: 2
       (D) OTHER INFORMATION: /note= "Val in position 2 is
            optionally modified with a lower alkyl or a lower
            alkanoyl when Xaa in the first position is absent."

(ix) FEATURE:
       (A) NAME/KEY: Modified-site
       (B) LOCATION: 5
       (D) OTHER INFORMATION: /note= "The 5th position amino acid
            can be Arg, Lys Ser or Asn"

(ix) FEATURE:
       (A) NAME/KEY: Modified-site
       (B) LOCATION: 8
       (D) OTHER INFORMATION: /note= "Pro in position 8 is
            optionally amidated, when it is the C terminal amino
            acid."

(ix) FEATURE:
       (A) NAME/KEY: Modified-site
       (B) LOCATION: 9
       (D) OTHER INFORMATION: /note= "The 9th position amino acid
            may be absent or a sequence of 1-14 amino acids amidated
            at the carboxyl terminus."

(xi) SEQUENCE DESCRIPTION: SEQ ID NO: 36:

Xaa Val Asp Pro Xaa Leu Glu Pro Xaa
 1               5

(2) INFORMATION FOR SEQ ID NO: 37:

(i) SEQUENCE CHARACTERISTICS:
       (A) LENGTH: 13 amino acids
       (B) TYPE: amino acid
       (C) STRANDEDNESS: <Unknown>
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Xaa in the first position
            may be absent or may be optionally 1-5 amino acids,
            optionally modified with a lower alkyl or lower alkanoyl
            at the N terminus."

(ix) FEATURE:
       (A) NAME/KEY: Modified-site
       (B) LOCATION: 2
       (D) OTHER INFORMATION: /note= "Lys in position 2 is
            optionally modified with a lower alkyl or a lower
            alkanoyl, when the first position Xaa is absent."

(ix) FEATURE:
       (A) NAME/KEY: Modified-site
       (B) LOCATION: 3
       (D) OTHER INFORMATION: /note= "The 3rd position amino acid
            can be either Gly or Ala."

(ix) FEATURE:
       (A) NAME/KEY: Modified-site
       (B) LOCATION: 12
       (D) OTHER INFORMATION: /note= "Lys in position 12 is
            optionally amidated, when it is the C terminal amino
            acid."

(ix) FEATURE:
       (A) NAME/KEY: Modified-site
       (B) LOCATION: 13
       (D) OTHER INFORMATION: /note= "The 13th position amino
            acid may be absent or may be a sequence of 1-5 additional
            amino acids, optionally substituted with an amide."
```

(xi) SEQUENCE DESCRIPTION: SEQ ID NO: 37:

Xaa Lys Xaa Leu Gly Ile Ser Tyr Gly Arg Lys Lys Xaa
1               5                   10

(2) INFORMATION FOR SEQ ID NO: 38:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The first position Xaa can
            be absent or a sequence of 1-3 aa, optionally modified
            with a lower alkyl or lower alkanoyl; or it can be Gln-
            Arg, optionally modified with a lower alkyl or lower
            alkanoyl."

(ix) FEATURE:
        (A) NAME/KEY: Modified-site
        (B) LOCATION: 2
        (D) OTHER INFORMATION: /note= "Arg in position 2 is
            optionally modified with a lower alkyl or a lower
            alkanoyl, when it is the N terminal amino acid."

(ix) FEATURE:
        (A) NAME/KEY: Modified-site
        (B) LOCATION: 4
        (D) OTHER INFORMATION: /note= "The 4th position amino acid
            can be Ala, Pro, Ser or Gln."

(ix) FEATURE:
        (A) NAME/KEY: Modified-site
        (B) LOCATION: 5
        (D) OTHER INFORMATION: /note= "The 5th position amino acid
            can be Pro or His."

(ix) FEATURE:
        (A) NAME/KEY: Modified-site
        (B) LOCATION: 6
        (D) OTHER INFORMATION: /note= "The 6th position amino acid
            can be Gln or Pro."

(ix) FEATURE:
        (A) NAME/KEY: Modified-site
        (B) LOCATION: 7
        (D) OTHER INFORMATION: /note= "The 7th position amino acid
            can be Asp, Asn, Gly or Ser."

(ix) FEATURE:
        (A) NAME/KEY: Modified-site
        (B) LOCATION: 8
        (D) OTHER INFORMATION: /note= "Ser in position 8 is
            optionally amidated."

(xi) SEQUENCE DESCRIPTION: SEQ ID NO: 38:

Xaa Arg Arg Xaa Xaa Xaa Xaa Ser
1               5

(2) INFORMATION FOR SEQ ID NO: 39:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide

```
    (ix) FEATURE:
         (A) NAME/KEY: Modified-site
         (B) LOCATION: 1
         (D) OTHER INFORMATION: /note= "Xaa in the first position
             can be absent or is optionally 1-3 amino acids,
             optionally modified with a lower alkyl or lower
             alkanoyl."

(ix) FEATURE:
         (A) NAME/KEY: Modified-site
         (B) LOCATION: 2
         (D) OTHER INFORMATION: /note= "Ser in position 2 is
             optionally modified with a lower alkyl or lower alkanoyl,
             when it is the N terminal amino acid."

(ix) FEATURE:
         (A) NAME/KEY: Modified-site
         (B) LOCATION: 4
         (D) OTHER INFORMATION: /note= "The 4th position amino acid
             can be Asn or Thr."

(ix) FEATURE:
         (A) NAME/KEY: Modified-site
         (B) LOCATION: 7
         (D) OTHER INFORMATION: /note= "The 7th position amino acid
             can be Ala or Val."

(ix) FEATURE:
         (A) NAME/KEY: Modified-site
         (B) LOCATION: 13
         (D) OTHER INFORMATION: /note= "Pro in position 13 is
             optionally amidated when it is the C terminal amino
             acid."

(ix) FEATURE:
         (A) NAME/KEY: Modified-site
         (B) LOCATION: 14
         (D) OTHER INFORMATION: /note= "Xaa in position 14 can be
             absent or is optionally 1-3 amino acids, optionally
             substituted with an amide."

(xi) SEQUENCE DESCRIPTION: SEQ ID NO: 39:

Xaa Ser Gln Xaa His Gln Xaa Ser Leu Ser Lys Gln Pro Xaa
1               5                   10

(2) INFORMATION FOR SEQ ID NO: 40:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 40:

Ser Gln Thr His Gln Ala Ser Leu Ser Lys Gln Pro
1               5                   10

(2) INFORMATION FOR SEQ ID NO: 41:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

Asp His Arg Leu Glu Pro
1               5
```

```
(2) INFORMATION FOR SEQ ID NO: 42:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

Asp Pro Asn Leu Asp Pro
1               5

(2) INFORMATION FOR SEQ ID NO: 43:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 43:

Asp Pro Asn Ile Glu Pro
1               5

(2) INFORMATION FOR SEQ ID NO: 44:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 44:

Asp Pro Asn Leu Glu Ser
1               5

(2) INFORMATION FOR SEQ ID NO: 45:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 45:

Val Asp Pro Lys Leu Glu Pro Trp Lys His Pro Gly Ser
1               5                   10

(2) INFORMATION FOR SEQ ID NO: 46:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

Val Asp Pro Ser Leu Glu Pro Trp Lys His Pro Gly Ser
1               5                   10
```

-continued

```
(2) INFORMATION FOR SEQ ID NO: 47:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 47:

Val Asp Pro Asn Leu Glu Pro Trp Lys His Pro Gly Ser
1               5                   10

(2) INFORMATION FOR SEQ ID NO: 48:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 48:

Val Asn Pro Ser Leu Glu Pro Trp Lys His Pro Gly Ser
1               5                   10

(2) INFORMATION FOR SEQ ID NO: 49:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 49:

Val Asp His Arg Leu Glu Pro Trp Lys His Pro Gly Ser
1               5                   10

(2) INFORMATION FOR SEQ ID NO: 50:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

Arg Arg Ala Pro Pro Asp Asn
1               5

(2) INFORMATION FOR SEQ ID NO: 51:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 51:

Arg Arg Ala Pro Gln Gly Asn
1               5
```

(2) INFORMATION FOR SEQ ID NO: 52:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 52:

```
Arg Gln Arg Arg Arg Ala His Gln Asn Ser
1               5                   10
```

(2) INFORMATION FOR SEQ ID NO: 53:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 53:

```
Arg Gln Arg Arg Arg Pro Pro Gln Asp Ser
1               5                   10
```

(2) INFORMATION FOR SEQ ID NO: 54:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 54:

```
Met Glu Pro Val Asp Pro Arg Leu Glu Pro Trp Lys His Pro Gly Ser
1               5                   10                  15

Gln Pro Lys Thr Ala
            20
```

(2) INFORMATION FOR SEQ ID NO: 55:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 55:

```
Phe Ile Thr Lys Gly Leu Gly Ile Ser Tyr Gly Arg Lys Lys Arg Arg
1               5                   10                  15

Gln Arg Arg Arg Ala Pro Gln Asp Ser Gln Thr His Gln Val Ser Leu
                20                  25                  30

Ser Lys Gln Pro
            35
```

(2) INFORMATION FOR SEQ ID NO: 56:

(i) SEQUENCE CHARACTERISTICS:
        (A) LENGTH: 9 amino acids

```
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 56:

Glu Pro Val Asp Pro Lys Leu Glu Pro
1               5

(2) INFORMATION FOR SEQ ID NO: 57:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 57:

Val Asp Pro Lys Leu Gly Pro
1               5

(2) INFORMATION FOR SEQ ID NO: 58:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Amino acid in position 4
            can be Arg, Lys, Ser or Asn."

(xi) SEQUENCE DESCRIPTION: SEQ ID NO: 58:

Val Asp Pro Xaa Leu Glu Pro Tyr Lys His Pro Gly Ser
1               5                   10

(2) INFORMATION FOR SEQ ID NO: 59:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 59:

Arg Gln Arg Arg Arg Pro Pro Gln Gly Ser
1               5                   10

(2) INFORMATION FOR SEQ ID NO: 60:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 60:

Arg Gln Arg Arg Gly Pro Pro Gln Gly Ser
```

```
1               5                   10
```

(2) INFORMATION FOR SEQ ID NO: 61:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 61:

```
Arg Gln Arg Arg Arg Pro Pro Gln Asn Ser
1               5                   10
```

(2) INFORMATION FOR SEQ ID NO: 62:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 62:

```
Arg Gln Arg Arg Arg Ser Pro Gln Asp Ser
1               5                   10
```

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 63:

```
Arg Gln Arg Arg Arg Ser Pro Gln Asn Ser
1               5                   10
```

(2) INFORMATION FOR SEQ ID NO: 64:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 64:

```
Arg Gln Arg Arg Arg Thr Pro Gln Ser Ser
1               5                   10
```

(2) INFORMATION FOR SEQ ID NO: 65:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 65:

```
Arg Gln Arg Arg Arg Ala His Gln Asp Ser
1               5                   10
```

(2) INFORMATION FOR SEQ ID NO: 66:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 66:

```
Arg Gln Arg Arg Arg Ala Pro Pro Asp Ser
1               5                   10
```

(2) INFORMATION FOR SEQ ID NO: 67:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "An amide is attached to the
            Lys in position 22."

(xi) SEQUENCE DESCRIPTION: SEQ ID NO: 67:

```
Cys Glu Pro Val Asp Pro Lys Leu Glu Pro Trp Lys Glu Leu Gly Ile
1               5                   10                  15

Ser Tyr Gly Arg Lys Lys
            20
```

(2) INFORMATION FOR SEQ ID NO: 68:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 68:

```
Arg Arg Thr Pro Gln Gly Ser
1               5
```

(2) INFORMATION FOR SEQ ID NO: 69:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 69:

```
Arg Arg Ala Pro Gln Gly Ser
1               5
```

(2) INFORMATION FOR SEQ ID NO: 70:

```
    (i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 70:

Arg Arg Thr Pro Gln Asp Ser
1               5

(2) INFORMATION FOR SEQ ID NO: 71:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 71:

Val Asp Pro Arg Leu Glu Pro Trp Lys His Pro Gly Ser Gln Pro Lys
1               5                   10                  15
Thr Ala (2) INFORMATION FOR SEQ ID NO: 72:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 72:

Arg Arg Ala Pro Gln Asn Ser
1               5

(2) INFORMATION FOR SEQ ID NO: 73:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 73:

Arg Arg Ser Pro Gln Asp Ser
1               5

(2) INFORMATION FOR SEQ ID NO: 74:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 74:

Cys Arg Gln Arg Arg Ala Pro Gln Asp Ser
1               5                   10
```

(2) INFORMATION FOR SEQ ID NO: 75:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 75:

Arg Arg Pro Pro Gln Asp Ser
1               5

(2) INFORMATION FOR SEQ ID NO: 76:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 76:

Arg Arg Pro Pro Gln Asn Ser
1               5

(2) INFORMATION FOR SEQ ID NO: 77:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 77:

Arg Arg Pro Pro Gln Gly Ser
1               5

(2) INFORMATION FOR SEQ ID NO: 78:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 78:

Arg Arg Ser Pro Gln Asn Ser
1               5

(2) INFORMATION FOR SEQ ID NO: 79:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 79:

Arg Arg Ala Pro Gln Ser Ser
1               5

(2) INFORMATION FOR SEQ ID NO: 80:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 80:

Arg Arg Ser Pro Gln Gly Ser
1               5

(2) INFORMATION FOR SEQ ID NO: 81:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 81:

Arg Arg Thr Pro Gln Asn Ser
1               5

(2) INFORMATION FOR SEQ ID NO: 82:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 82:

Arg Gln Arg Gln Arg Ala Pro Asp Ser Ser
1               5                   10

(2) INFORMATION FOR SEQ ID NO: 83:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 83:

Arg Gln Arg Arg Arg Ala Pro Glu Asp Ser
1               5                   10

(2) INFORMATION FOR SEQ ID NO: 84:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Binding-site
        (B) LOCATION: 13

(D) OTHER INFORMATION: /note= "an amide is attached to the
            Ser in position 13"

(xi) SEQUENCE DESCRIPTION: SEQ ID NO: 84:

Cys Val Asp Pro Asn Leu Glu Pro Trp His Pro Gly Ser
1               5                   10

(2) INFORMATION FOR SEQ ID NO: 85:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 85:

Ser Gly Ser Gly Val Asp Pro Asn Leu Glu Pro Trp Lys His Pro Gly
1               5                   10                  15
Ser (2) INFORMATION FOR SEQ ID NO: 86:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Amino acid in position 4
            can be Arg, Lys, Ser or Asn."

(xi) SEQUENCE DESCRIPTION: SEQ ID NO: 86:

Val Asp Pro Xaa Leu Glu Pro
1               5

(2) INFORMATION FOR SEQ ID NO: 87:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Amino acid in position 2
            can be Gly or Ala"

(xi) SEQUENCE DESCRIPTION: SEQ ID NO: 87:

Lys Xaa Leu Gly Ile Ser Tyr Gly Arg Lys Lys
1               5                   10

(2) INFORMATION FOR SEQ ID NO: 88:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear

```
    (ii) MOLECULE TYPE: peptide (ix) FEATURE:
         (A) NAME/KEY: Modified-site
         (B) LOCATION: 3
         (D) OTHER INFORMATION: /note= "Amino acid in position 3
             can be Ala, Pro, Ser or Gln."

(ix) FEATURE:
         (A) NAME/KEY: Modified-site
         (B) LOCATION: 4
         (D) OTHER INFORMATION: /note= "Amino acid in position 4
             can be Pro or His."

(ix) FEATURE:
         (A) NAME/KEY: Modified-site
         (B) LOCATION: 5
         (D) OTHER INFORMATION: /note= "Amino acid in position 5
             can be Gln or Pro."

(ix) FEATURE:
         (A) NAME/KEY: Modified-site
         (B) LOCATION: 6
         (D) OTHER INFORMATION: /note= "Amino acid in position 6
             can be Asp, Asn, Gly or Ser."

(xi) SEQUENCE DESCRIPTION: SEQ ID NO: 88:

Arg Arg Xaa Xaa Xaa Xaa Ser
1               5

(2) INFORMATION FOR SEQ ID NO: 89:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /note= "Amino acid in position 3
             can be Asn or Thr."

(ix) FEATURE:
         (A) NAME/KEY: Modified-site
         (B) LOCATION: 6
         (D) OTHER INFORMATION: /note= "Amino acid in position 6
             can be Ala or Val."

(xi) SEQUENCE DESCRIPTION: SEQ ID NO: 89:

Ser Gln Xaa His Gln Xaa Ser Leu Ser Lys Gln Pro
1               5                   10

(2) INFORMATION FOR SEQ ID NO: 90:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 90:

Gly Ser Gly Ser
1

(2) INFORMATION FOR SEQ ID NO: 91:

(i) SEQUENCE CHARACTERISTICS:
```

(A) LENGTH: 4 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "Biocytin-amide is attached
                to Ser in position 4."

(xi) SEQUENCE DESCRIPTION: SEQ ID NO: 91:

Gly Ser Gly Ser
1

(2) INFORMATION FOR SEQ ID NO: 92:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 8
            (D) OTHER INFORMATION: /note= "NH2 is attached to the Trp
                in position 8"

(xi) SEQUENCE DESCRIPTION: SEQ ID NO: 92:

Val Asp Pro Arg Leu Glu Pro Trp
1               5

(2) INFORMATION FOR SEQ ID NO: 93:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /note= "NH2 is attached to Pro in
                position 7"

(xi) SEQUENCE DESCRIPTION: SEQ ID NO: 93:

Val Asp Pro Arg Leu Glu Pro
1               5

(2) INFORMATION FOR SEQ ID NO: 94:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /note= "NH2 is attached to the Glu
                in position 6"

(xi) SEQUENCE DESCRIPTION: SEQ ID NO: 94:

Val Asp Pro Arg Leu Glu
1               5

(2) INFORMATION FOR SEQ ID NO: 95:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 95:

Val Asp Pro Arg Leu
1               5

(2) INFORMATION FOR SEQ ID NO: 96:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 96:

Asp Pro Arg Leu Glu Pro Trp
1               5

(2) INFORMATION FOR SEQ ID NO: 97:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 97:

Gly Pro Arg Leu Glu Pro
1               5

(2) INFORMATION FOR SEQ ID NO: 98:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 98:

Ala Pro Arg Leu Glu Pro
1               5

(2) INFORMATION FOR SEQ ID NO: 99:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 99:

Glu Pro Val Asp Pro Arg Leu Glu Pro Trp Lys His Pro Gly Ser
1               5                   10                  15

(2) INFORMATION FOR SEQ ID NO: 100:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 100:

Val Asp Pro Arg Leu Glu Pro Trp Lys His Pro
1               5                   10

(2) INFORMATION FOR SEQ ID NO: 101:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 101:

Val Asp Pro Arg Leu Glu Pro Trp Lys
1               5

(2) INFORMATION FOR SEQ ID NO: 102:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /note= "NH2 is attached to Pro in
            position 7"

(xi) SEQUENCE DESCRIPTION: SEQ ID NO: 102:

Val Asp Pro Arg Leu Glu Pro
1               5

(2) INFORMATION FOR SEQ ID NO: 103:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 103:

Met Asp Pro Val Asp Pro Arg Leu Glu Pro
1               5                   10

(2) INFORMATION FOR SEQ ID NO: 104:

```
    (i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 104:

Met Asp Pro Val Asp Pro Arg Leu Glu Pro Trp Lys
1               5                   10

(2) INFORMATION FOR SEQ ID NO: 105:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 105:

Phe Ile Thr Lys Gly Leu Gly Ile Ser Tyr Gly Arg Lys Lys Arg Arg
1               5                   10                  15

Gln Arg (2) INFORMATION FOR SEQ ID NO: 106:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 106:

Lys Ala Leu Gly Ile Ser Tyr Gly Arg Lys Lys
1               5                   10

(2) INFORMATION FOR SEQ ID NO: 107:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /note= "NH2 is attached to Ser in
            position 10"

(xi) SEQUENCE DESCRIPTION: SEQ ID NO: 107:

Arg Gln Arg Arg Arg Ala Pro Gln Asp Ser
1               5                   10

(2) INFORMATION FOR SEQ ID NO: 108:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide
```

```
    (ix) FEATURE:
         (A) NAME/KEY: Modified-site
         (B) LOCATION: 8
         (D) OTHER INFORMATION: /note= "NH2 is attached to Ser in
             position 8"

(xi) SEQUENCE DESCRIPTION: SEQ ID NO: 108:

Gly Arg Arg Ala Pro Gln Asp Ser
 1               5

(2) INFORMATION FOR SEQ ID NO: 109:

(i) SEQUENCE CHARACTERISTICS:
         (A) LENGTH: 11 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Modified-site
         (B) LOCATION: 11
         (D) OTHER INFORMATION: /note= "NH2 is attached to Gln in
             position 11"

(xi) SEQUENCE DESCRIPTION: SEQ ID NO: 109:

Arg Arg Ala Pro Gln Asp Ser Gln Thr His Gln
 1               5                  10

(2) INFORMATION FOR SEQ ID NO: 110:

(i) SEQUENCE CHARACTERISTICS:
         (A) LENGTH: 7 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /note= "Amino acid in position 3
             can be Ala, Pro, Ser or Gln"

(ix) FEATURE:
         (A) NAME/KEY: Modified-site
         (B) LOCATION: 6
         (D) OTHER INFORMATION: /note= "Amino acid in position 6
             can be Asp, Asn, Gly or Ser"

(xi) SEQUENCE DESCRIPTION: SEQ ID NO: 110:

Arg Arg Xaa Pro Gln Xaa Ser
 1               5

(2) INFORMATION FOR SEQ ID NO: 111:

(i) SEQUENCE CHARACTERISTICS:
         (A) LENGTH: 13 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 111:

Ser Gln Thr His Gln Val Ser Leu Ser Lys Gln Pro Cys
 1               5                  10
```

(2) INFORMATION FOR SEQ ID NO: 112:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 112:

Ser Gln Thr His Gln Val Ser Leu Ser Lys Gln Pro
1              5                  10

(2) INFORMATION FOR SEQ ID NO: 113:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 113:

Ser Gln Asn His Gln Val Ser Leu Ser Lys Gln Pro
1              5                  10

(2) INFORMATION FOR SEQ ID NO: 114:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 114:

Ser Gln Thr His Gln Ala Ser Leu Ser Lys Gln Pro
1              5                  10

(2) INFORMATION FOR SEQ ID NO: 115:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 115:

Val Asp Pro Asn Leu Glu Pro Trp Lys His Pro Gly Ser
1              5                  10

(2) INFORMATION FOR SEQ ID NO: 116:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /note= "An amide is attached to Ser
            in position 14"

(xi) SEQUENCE DESCRIPTION: SEQ ID NO: 116:

Cys Val Asp Pro Asn Leu Glu Pro Trp Lys His Pro Gly Ser
1               5                  10

(2) INFORMATION FOR SEQ ID NO: 117:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 117:

Cys Arg Gln Arg Arg Arg Ala Pro Asp Ser Ser Gln Asn His Gln
1               5                  10                  15

(2) INFORMATION FOR SEQ ID NO: 118:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 118:

Glu Pro Val Asp Pro Lys Leu Glu Pro
1               5

(2) INFORMATION FOR SEQ ID NO: 119:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 119:

Glu Pro Val Asp Pro Ser Leu Glu Pro
1               5

(2) INFORMATION FOR SEQ ID NO: 120:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 120:

Glu Pro Val Asp Pro Asn Leu Glu Pro
1               5

(2) INFORMATION FOR SEQ ID NO: 121:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear -continued

```
    (ii) MOLECULE TYPE: peptide (xi) SEQUENCE DESCRIPTION: SEQ ID NO: 121:

Arg Arg Ala His Gln Asp Ser
1               5

(2) INFORMATION FOR SEQ ID NO: 122:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 122:

Ser Gln Thr His Gln Val Ser Leu Ser Lys Gln Pro
1               5                   10

(2) INFORMATION FOR SEQ ID NO: 123:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Biotin is attached to Ser
            in position 1"

(xi) SEQUENCE DESCRIPTION: SEQ ID NO: 123:

Ser Gly Ser Gly
1

(2) INFORMATION FOR SEQ ID NO: 124:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /note= "Amino acid in position 7
            can be Arg, Lys Ser or Asn"

(xi) SEQUENCE DESCRIPTION: SEQ ID NO: 124:

Glu Pro Val Asp Pro Xaa Leu Glu Pro
1               5
```